_United States Patent_ [19]

Beattie et al.

[11] 4,255,423

[45] Mar. 10, 1981

[54] CEPHALOSPORIN COMPOUNDS

[75] Inventors: Thomas R. Beattie, North Plainfield; John Hannah, Matawan; David B. R. Johnston, Warren, all of N.J.

[73] Assignee: Merck & Co., Inc., Rahway, N.J.

[21] Appl. No.: 819,511

[22] Filed: Jul. 27, 1977

Related U.S. Application Data

[63] Continuation of Ser. No. 624,623, Oct. 22, 1975, abandoned, which is a continuation of Ser. No. 367,291, Jun. 5, 1973, abandoned.

[51] Int. Cl.[3] ............................................ C07D 501/20
[52] U.S. Cl. ..................................... 424/246; 544/16; 544/21; 544/22; 544/28; 542/434; 542/436; 542/437; 542/442; 542/443; 542/444; 542/445; 542/446
[58] Field of Search ....................... 544/16, 22, 21, 24, 544/25, 28; 424/246

[56] References Cited

U.S. PATENT DOCUMENTS

| | | | |
|---|---|---|---|
| 3,769,277 | 10/1973 | Long et al. | 544/16 |
| 3,994,884 | 11/1976 | Weir | 544/22 |
| 4,032,521 | 6/1977 | Christensen et al. | 544/21 |
| 4,147,863 | 4/1979 | Miyadera et al. | 542/346 |

_Primary Examiner_—Nicholas S. Rizzo
_Attorney, Agent, or Firm_—James A. Arno; Julian S. Levitt

[57] ABSTRACT

Novel cephalosporin compounds having a substituted or unsubstituted vinyl group at the 3-position are prepared by the reaction of a phosphoranylidene compound with a compound containing a carbonyl group. The novel cephalosporin compounds are active against a range of gram-negative and gram-positive microorganisms and are of value in human and veterinary medicine.

8 Claims, No Drawings

CEPHALOSPORIN COMPOUNDS

This is a continuation of application Ser. No. 624,623 filed 10-22-75 now abandoned which in turn a continuatin of U.S. Ser. No. 367,291 filed June 5, 1973, now abandoned.

BACKGROUND OF THE INVENTION

This invention relates to new antibacterial substances and processes for their preparation. More particularly, it is concerned with novel 3-cephem compounds containing a 3-vinyl group, and with intermediates and processes useful in their preparation.

In the past several decades, various antibiotic substances have proven to be invaluable in treatment and control of various infections. However, new antibiotics are constantly being sought in order to supplement and expand the physicians armamentarium, particularly for the treatment of infections involving pathogens which have become resistant to the chemotherapeutic agents now in use.

Prior Art of Interest

German Offenlegungsschrift No. 2,103,014.

Summary of the Invention

It is therefore an object of this invention to provide novel antibiotic substances and processes for their synthesis. Another object is to provide processes and intermediates useful in the synthesis of the novel antibiotics. Other objects will be apparent from the detailed description hereinafter provided.

The novel 3-vinyl compounds of this invention can be represented by the structural formula

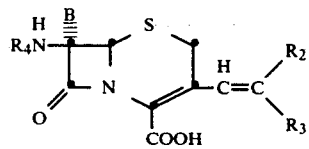

wherein $R_4$ represents an acyl group, preferably a carboxylic acid acyl group that is conventionally employed in the penicillin and cephalosporin art;

B is hydrogen or methoxy;

wherein when B is methoxy:

$R_2$ and $R_3$ may be the same or different and are each selected from the following:

(a) hydrogen;

(b) aryl (eg. phenyl, styryl, benzyl, phenethyl, trityl, cinnamyl, mesityl, tolyl, cumenyl, xylyl including substituted aryl hydrocarbons wherein the substituents may be

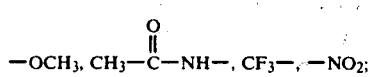

halo, hydroxyl, $NH_2$; etc.;

(c) heterocyclic aromatic, particularly a 5 or 6 membered heterocyclic group containing at least one hetero atom selected from S, N and O, eg. thienyl, thiazolyl, furyl, pyranyl, pyrrolyl, imidazolyl, pyrazolyl, pyridyl, pyrazinyl, pyrimidinyl, pyridazinyl, isothiazolyl, isoxazolyl, pyrolidenyl, oxyazoloyl, 1,2,3-thiadiazolyl, 1-oxidopyridyl, tetrahydropyranzoyl, furazanoyl including substituted heterocyclic aromatic moieties wherein the substituents may be halo (eg. chloro, fluoro, bromo); lower alkyl of 1-6 cabon atoms (eg. methyl, ethyl, propyl, pentyl, hexyl,); trifluoromethyl; mono- and di-lower alkyl substituted sulfamyl (eg. dimethylsulfamyl, methylsulfamyl); nitro; lower alkoxy or 1-6 carbon atoms (methoxy, ethoxy, pentoxy, etc..); also included within the scope of heterocyclic aromatic are the substituted and unsubstituted fused ring hetero moieties such as quinoline, isoquinoline etc..;

(d) Alkyl, preferably lower alkyl of 1-6 carbon atoms such as methyl, ethyl, propyl, t-butyl, hexyl; including substituted alkyl wherein the substitutents may be halo (e.g. chloro, fluoro or bromo such as $CF_3$), hydroxyl, $NH_2$, $NO_2$, etc..;

(e) cycloaliphatic, preferably monocyclic hydrocarbons of 3-6 carbon atoms (eg. cyclopropyl, cyclohexyl, cyclopentyl, cyclopentenyl, cyclopentadienyl etc..);

(f) carboxyl
(g) cyano
(h) $-SO_2NR_4'R_5'$
(i) $-P(O)(OR_4')_2$ (j) $-\overset{O}{\underset{\|}{C}}-N(R_4')_2$ (k) $-\overset{O}{\underset{\|}{C}}-OR_4'$ wherein $R'_4$ and $R'_5$ are selected from hydrogen, lower alkyl of 1-6 carbon atoms and aryl (e.g. phenyl, styryl, benzyl, phenylethyl, tolyl, etc..), including aryl groups which may be substituted by halo (chloro, bromo, fluoro); —OH, amino, trifluoromethyl, alkyl of 1-6 carbon atoms and the like;

(l) heterocyclic aliphatic, particularly a 5 or 6 membered heterocyclic aliphatic group containing at least one atom selected from O, N and S (e.g.

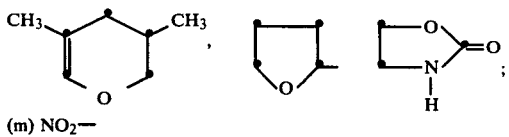

(m) $NO_2-$ (n) alkanoyloxyalkyl wherein the alkanoyl moiety is straight or branched and has 1-6 carbon atoms and the alkyl portion has 1-6 carbon atoms such as acetoxymethyl, pivaloyloxymethyl, acetoxyethyl, propionyloxyethyl, acetoxypropyl, etc.

wherein when B is hydrogen:

$R_2$ and $R_3$ may be the same or different and are each selected from the following:

(a) heterocyclic aromatic, particularly a 5 or 6 membered heterocyclic group containing at least one hetero atom selected from S, N and O, e.g. thienyl, thiazolyl, furyl, pyranyl, pyrrolyl, imidazolyl, pyrazolyl, pyridyl, pyrazinyl, pyrimidinyl, pyridazinyl, isothiazolyl, isoxazolyl, furazanyl including substituted heterocyclic aromatic wherein the substituents may be halo (e.g. chloro, fluoro, bromo); lower alkyl of 1-6 carbon atoms (e.g. methyl, ethyl, propyl, pentyl, hexyl); trifluoromethyl; mono- and di-lower alkyl substituted sulfamyl (eg. dimethylsulfamyl, methylsulfamyl), nitro; lower alkoxy of 1-6 carbon atoms (methoxy, ethoxy, pentoxy etc.); also included within the scope of heterocyclic aromatic are the substituted and unsubstituted fused ring hetero moieties such as quinoline, isoquinoline, etc..;

(b) —SO$_2$NR$_4$'R$_5$'
(c) —P(O) (OR$_4$')$_2$
(d) —C(=O)—N(R$_4$')$_2$ wherein R'$_4$ and R'$_5$ are the same or different and are selected from hydrogen lower alkyl of 1–6 carbon atoms and aryl (eg. phenyl, sytryl, benzyl, phenylethyl, tolyl etc. including aryl groups which may be substituted by halo (chloro, bromo, fluoro); —OH; amino; trifluoromethyl; alkyl of 1–6 carbon atoms and the like.

(e) heterocyclic aliphatic group, particularly a 5 or 6 membered heterocyclic aliphatic group containing at least one atom selected from O, N and S (eg.

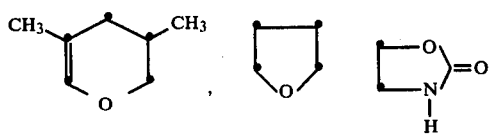

(f) NO$_2$—.

(g) alkanoyloxyalkyl wherein the alkanoyl moiety is straight or branched and has 1–6 carbon atoms and the alkyl portion has 1–6 carbon atoms such as acetoxymethyl, pivaloyloxymethyl, acetoxyethyl, propionyloxyethyl, acetoxypropyl, etc.

(h) hydrogen with the proviso that both R$_2$ and R$_3$ may not be hydrogen.

The acyl radical represented by R$_4$ can be a substituted or unsubstituted aliphatic, aromatic or heterocyclic, araliphatic or heterocyclyaliphatic carboxylic acid radical or a carbothioic acid radical such as the acyl radicals of the known cephalosporins and penicillins. These acyl radicals can be represented by the general formula

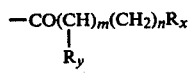

where R$_y$ is a radical of the group defined below, m and n represent 0–4 and R$_x$ represents R" or ZR", which are defined below.

The following compilation of acyl groups illustrated below are merely representative and not intended to be exhaustive.

One group of acyl radicals can be represented by the acyl group general formula:

wherein R" represents a substituted or unsubstituted straight or branched chain alkyl, alkenyl or alkynyl group; aryl, aralkyl; cycloalkyl; or a heteroaryl or heteroaralkyl group. These groups can be unsubstituted or can be substituted by radicals such as alkyl, akoxy, halo, cyano, carboxy, sulfoamino, carbamoyl, sulfonyl, azido, amino, substituted amino, haloalkyl, carboxyalkyl, carbamoylalkyl, N-substituted carbamoylalkyl, guanidino, N-substituted guanidino, quanidinoalkyl, and the like. Representative examples of such acyl groups that might be mentioned are those wherein R" is benzyl, p-hydroxybenzyl, 4-amino-4-carboxybutyl, methyl, cyanomethyl, 2-pentenyl, n-amyl, n-heptyl, ethyl, 3- or 4-nitrobenzyl, phenethyl, β,β-diphenylethyl, methyldiphenylmethyl, triphenylmethyl, 2-methoxyphenyl, 2,6-dimethoxyphenyl, 2,4,6-trimethoxyphenyl, 3,5-dimethyl-4-isozazolyl, 3-butyl-5-methyl-4-isoxazolyl, 5-methyl-3-phenyl-4-isoxazolyl, 3-(2-chlorophenyl)-5-methyl-4-isoxazolyl, 3-(2-dichlorophenyl)-5-methyl-4-isoxazolyl, D-4-amino-4-carboxybutyl, D-4-N-benzoylamino-4-carboxy-n-butyl, p-aminobenzyl, o-aminobenzyl, m-aminobenzyl, (3-pyridyl)methyl, 2-ethoxy-1-naphthyl, 3-carboxy-2-quinoxalinyl, 3-(2,6-dichlorophenyl)-5-(2-furyl)-4-isoxazolyl, 3-phenyl-4-isoxazolyl, 5-methyl-3-(4-guanidinophenyl)-4-isoxazolyl, 4-guanidinomethylphenyl, 4-guanidinomethylbenzyl, 4-guanidinobenzyl, 4-guanidinophenyl, 2,6-dimethoxy-4-guanidinophenyl, o-sulfobenzyl, p-carboxymethylbenzyl, p-carbamoylmethylbenzyl, m-fluorobenzyl, m-bromobenzyl, p-chlorobenzyl, p-methoxybenzyl, 1-naphthylmethyl, 3-isothiazolylmethyl, 4-isothiazolylmethyl, 5-isothiazolylmethyl, 4-pyridylmethyl, 5-isoxazolylmethyl, 4-methoxy-5-isoxazolylmethyl, 4-methyl-5-isoxazolylmethyl, 1-imidazolylmethyl, 2-benzofuranylmethyl, 2-indolylmethyl, 2-phenylvinyl, 2-phenylethynyl, 2-(5-nitrofuranyl)vinyl, phenyl, o-methoxyphenyl, o-chlorophenyl, o-phenylphenyl, p-aminomethylbenzyl, 1-(5-cyanotriazolyl)methyl, difluoromethyl, dichloromethyl, dibromomethyl, 1-(3-methylimidazolyl)methyl, 2- or 3-(5-carboxymethylthienyl)methyl, 2- or 3-(4-carbamoylthienyl) methyl, 2- or 3-(5-methylthienyl)-methyl, 2- or 3-(5-methoxythienyl)methyl, 2- or 3-(4-chlorothienyl)methyl, 2- or 3-(5-sulfothienyl)methyl, 2- or 3-(5-carboxythienyl)methyl, 3-(1,2,5-thiadiazolyl)-methyl, 3-(4-methoxy-1,2,5-thiadiazolyl)methyl, 2-furylmethyl, 2-(5-nitrofuryl)methyl, 3-furylmethyl, 2-thienylmethyl, 3-thienylmethyl, and tetrazolylmethyl.

The acyl group can also be a radical of the formula

wherein n is 0–4, Z represents oxygen or sulfur, and R" is defined as above. Representative members of the substituent

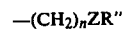

that might be mentioned are allylthiomethyl, phenylthiomethyl, butylmercaptomethyl, α-chlorocrotylmercaptomethyl, phenoxymethyl, phenoxyethyl, phenoxybutyl, phenoxybenzyl, diphenoxymethyl, dimethylmethoxymethyl, dimethylbutoxymethyl, dimethylphenoxymethyl, 4-guanidinophenoxymethyl, 4-pyridylthiomethyl, p-(carboxymethyl)phenoxymethyl, p-(carboxymethyl)phenylthiomethyl, 2-thiazolylthiomethyl, p-(sulfo)phenoxymethyl, p-(sulfo)phenylthiomethyl, p-(carboxy)phenoxymethyl, p-(carboxy)phenylthiomethyl, p-(carboxymethyl)phenoxymethyl, p-(carboxymethyl)phenylthiomethyl, 2-pyrimidinylthiomethyl, phenylthiomethyl, 1-(5,6,7,8-tetrahydronaphthyl)oxomethyl, 6,8-bis(methylthio)octanoyl.

Alternatively, the acyl group can be a radical of the formula

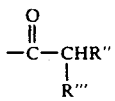

wherein R'' is defined as above and R''' is a radical such as amino, hydroxy, azido, carbamoyl, guanidino, acyloxy, halo, sulfamino, tetrazolyl, sulfo, carboxy, carbalkoxy, and the like. Representative members of the substituent

that might be mentioned are α-aminobenzyl, α-amino-2-thenyl, α-methylaminobenzyl, α-amino-γ-methylmercaptopropyl, α-amino-3 or 4-chlorobenzyl, α-amino-3 or 4-hydroxybenzyl, α-amino-2,4-dichlorobenzyl, α-amino-3,4-dichlorobenzyl, D(−)-α-hydroxybenzyl, α-carboxybenzyl, α-amino-3-thenyl, α-amino-2-thenyl, D(−)-α-amino-3-chloro-4-hydroxybenzyl, D(−)-α-amino-3-thenyl, 1-aminocyclohexyl, α-(5-tetrazolyl)-benzyl, α-sulfaminobenzyl, α-sulfamino-3-thenyl, α-(N-methylsulfamino)-benzyl, D(−)-α-guanidino-2-thenyl, D(−)-α-guanidionbenzyl, α-guanylureidobenzyl, α-hydroxybenzyl, α-azidobenzyl, α-fluorobenzyl, 4-(5-methoxy-1,3-oxadiazole)-aminomethyl, 4-(5-methoxy-1,3-oxadiazole)-hydroxymethyl, 4-(5-methoxy-1,3-oxadiazole)-carboxymethyl, 4-(5-methoxy-1,3-sulfadiazole)-aminomethyl, 4-(5-methoxy-1,3-sulfadiazole)-hydroxymethyl, 4-(5-methoxy-1,3-sulfadiazole)-carboxymethyl, 2-(5-chlorothienyl)-aminomethyl, 2-(5-chlorothienyl)-hydroxymethyl, 2-(5-chlorothienyl)-carboxymethyl, 3-(1,2-thiazole)-aminomethyl, 3-(1,2-thiazole)-hydroxymethyl, 3-(1,2-thiazole)-carboxymethyl, 2-(1,4-thiazolyl)-aminomethyl, 2-(1,4-thiazolyl)-hydroxymethyl, 2-(1,4-thiazolyl)-aminomethyl, 2-(1,4-thiazolyl)-hydroxymethyl, 2-(1,4-thiazoyly)-carboxymethyl, 2-benzothienylamino ethyl, 2-benzothienylhydroxymethyl, 2-benzothienylcarboxymethyl, 2-azidooctyl-3-phenyl-3-azidomethyl, α-sulfobenzyl, and α-phosphonobenzyl.

Alternatively, the group

can be a sulfonamido group such as phenylsulfonamido, ethylsulfonamido, benzylsulfonamido, 2,5-dimethylsulfonamido, 4-chlorosulfonamido, 4-chlorophenylsulfonamido, 4-methoxysulfonamido, and the like.

The acyl substituents of the general formula

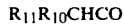

wherein $R_{10}$ and $R_{11}$ are as defined below represent a preferred group of substituents because of their generally useful antibiotic activity. $R_{10}$ represents hydrogen, halo, amino, guanidino, phosphono, hydroxy, tetrazolyl, carboxy, sulfo or sulfamino. $R_{11}$ represents phenyl, substituted phenyl, a monocyclic heterocyclic 5- or 6-membered ring containing one or more oxygen, sulfur or nitrogen atoms in the ring, substituted heterocycles, phenylthio, heterocyclic or substituted heterocylcic thio groups; or cyano. The substituents can be halo, carboxymethyl, guanidino, guanidinomethyl, carboxamidomethyl, aminomethyl, nitro, methoxy or methyl.

Examples of these preferred substituents that might be mentioned are phenacetyl, 3-bromophenylacetyl, p-aminomethylphenylacetyl, 4-carboxylmethylphenylacetyl, 4-carboxamidomethylphenylacetyl, 2-furylacetyl, 5-nitrofurylacetyl, 3-furylacetyl, 2-thienylacetyl, 5-chlorothienylacetyl, 5-methoxythienylacetyl, α-guanidino-2-thienylacetyl, 3-thienylacetyl, 4-methylthienylacetyl, 3-isothiazolylacetyl, 4-methoxyisothiazolylacetyl, 4-isothiazolylacetyl, 3-methylisothiazolylacetyl, 5-isothiazolylacetyl, 3-chloroisothiazolylacetyl, 3-methyl-1,2,5-oxidiazolylacetyl, 1,2,5-thiadiazolyl-4-acetyl, 3-methyl-1,2,5-thiadiazolyl-4-acetyl, 3-chloro-1,2,5-thiadiazolyl-4-acetyl, 3-methoxy-1,2,5-thiadiazolyl-4-acetyl, phenylthioacetyl, 4-pyridylthioacetyl, cyanoacetyl, tetrazolylacetyl, α-fluorophenylacetyl, D-phenylglycyl, 4-hydroxy-D-phenylglycyl, 2-thienylglycyl, 3-thienylglycyl, phenylmalonyl, 3-chlorophenylmalonyl, 2-thienylmalonyl, 3-thienylmalonyl, α-phosphonophenylacetyl, α-sulfaminophenylacetyl, α-hydroxyphenylacetyl, α-tetrazolylphenylacetyl and α-sulfophenylacetyl.

Pursuant to a preferred embodiment of this invention, $R_4$ is represented by the formula

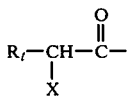

wherein X is hydrogen, halogen, amino, guanidino, phosphono, hydroxy, tetrazolyl, carboxy, sulfo, or sulfamino; $R_t$ is phenyl, substituted phenyl, a monocyclic heterocyclic 5- or 6-membered ring containing one or more oxygen, sulfur or nitrogen atoms in the ring, substituted heterocycles, phenylthio, phenyloxy, heterocyclic or substituted heterocyclic thio groups, lower alkyl (1–6 carbon atoms), or cyano; the substituents on the $R_t$ group being halo, carboxymethyl, guanidino, guanidinomethyl, carboxamidomethyl, aminomethyl, nitro, methoxy or methyl. Particularly preferred are acyl groups where X is hydrogen, hydroxy, amino or carboxy and $R_t$ is phenyl, lower alkyl or a 5- or 6-membered heterocyclic ring having one or two sulfur, oxygen or nitrogen hetero atoms. Specific $R_2$ substituents that might be mentioned as preferred include thiazolyl, thienyl, furyl and phenyl.

Also included within the scope of the invention are the non-toxic derivatives of the novel 3-vinyl cephem compounds. By the term "non-toxic" as applied to the compounds of the invention is meant those derivatives which are physiologically acceptable in the dosage at which they are administered. Such derivatives include salts and esters.

The cephalosporin compounds with which this invention is concerned are conveniently designated as "cepham" compounds containing the basic fused-ring betalactam thiazine structure

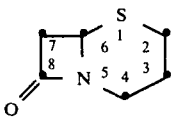

which is known as cepham. Thus, the cephalosporin compounds are called "cephem" referring to the basic structure with a single olefin bond.

The novel 3-vinyl cephalosporin compounds of the invention may be prepared by reacting a phosphoranylidene compound of the formula

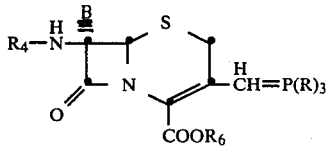

with a carbonyl compound of the formula R₂—CO—R₃;

wherein R₄ is a carboxylic acyl group conventionally employed in the penicillin and cephalosporin art;

B is hydrogen or methoxy;

R may be the same or different organo group and includes alkyl, aralkyl or aryl groups or such groups substituted by, for example, one or more halogen atoms, nitro groups, cyano groups, amino groups, acyl groups, acylamido groups and the like. Examples of R groups of interest include the lower alkyl e.g. methyl, ethyl, propyl or butyl; and phenyl or substituted phenyl; and benzyl;

$R_6$ is hydrogen or a carboxyl-blocking group;

and wherein $R_2$ and $R_3$ have the above defined meanings.

The carboxyl blocking group ($R_6$) is, preferably, an ester formed with an alcohol or phenol which may readily be split off at a later stage of the reaction.

Generally, it is preferred to carry out the reaction with a cephalosporin compound wherein the carboxy group is blocked or protected since maximum yields of the desired product are obtained with such derivatives. It is preferable that a protecting group be utilized which can be removed to obtain the free acid without disruption of the β-lactam moiety.

The group protecting the 4-carboxyl group may be formed with an alcohol (aliphatic or araliphatic), phenol, silanol, stannanol or acid which may readily be split off at a later stage of the reaction.

Suitable esters thus include compounds containing as the 4-ester group, a group selected from the following list which is representative and not intended to be an exhaustive list of possible ester groups:

(i)—COOCR$^a$R$^b$R$^c$ wherein at least one of R$^a$, R$^b$ and R$^c$ is an electron-donor e.g. p-methoxyphenyl, 2,2,6-trimethylphenyl, 9-anthryl, methoxy, acetoxy, tetrahydrofur-2-yl, tetrahydropyran-2-yl or fur-2-yl. The remaining R$^a$, R$^b$ and R$^c$ groups may be hydrogen or organic substituting groups. Suitable ester groups of this type include p-methoxybenzyloxycarbonyl and 2,4,6-trimethylbenzyloxycarbonyl.

(ii)—COOCR$^a$R$^b$R$^3$ wherein at least one of R$^a$, R$^b$ and R$^c$ is an electron-attracting group e.g. benzoyl, p-nitrophenyl, 4-pyridyl, trichloromethyl, tribromomethyl, iodomethyl, cyanomethyl, ethoxycarbonylmethyl, arylsulphonylmethyl, 2-dimethylsulphoniumethyl, o-nitrophenyl or cyano. The remaining R$^a$, R$^b$ and R$^c$ groups may be hydrogen or organic substituting groups. Suitable esters of this type include benzoylmethoxycarbonyl, p-nitrobenzyloxycarbonyl, 4-pyridylmethoxycarbonyl, 2,2,2-trichloroethoxycarbonyl and 2,2,2-tribromoethoxycarbonyl.

(iii)—COOCR$^a$R$^b$R$^c$ wherein at least two of R$^a$, R$^b$ and R$^c$ are hydrocarbon such as alkyl e.g. methyl or ethyl, or aryl e.g. phenyl and the remaining R$^a$, R$^b$ and R$^c$ group, if there is one, is hydrogen. Suitable esters of this type include, t-butyloxycarbonyl, t-amyloxycarbonyl, diphenylmethoxycarbonyl and triphenylmethoxycarbonyl.

(iv)—COOR$^d$ wherein R$^d$ is adamantyl, 2-benzyloxyphenyl, 4-methylthiophenyl or tetrahydropyran-2-yl.

Silyl esters may conveniently be prepared from a halosilane or a silazane of the formula R$^4$₃SiX; R$^4$₂SiX₂; R$^4$₃Si.NR$^4$₂; R$^4$₃SiR$^4$₃; R$^4$₃Si.NH.COR$^4$; R$^4$₃Si.NH.CO.NH.SiR$^4$₃; R$^4$NH.CO.NR$^4$.SiR$^4$₃; or R$^4$C(OSiR$^4$₃): NsiR$^4$₃ where X is a halogen and the various groups R$^4$, which can be the same or different, represent hydrogen atoms or alkyl, e.g. methyl, ethyl, n-propyl, iso-propyl; aryl, e.g. phenyl; or aralkyl e.g. benzyl groups.

Preferred derivatives of silanols are silyl chlorides such as for example trimethylchlorosilane and dimethyldichlorosilane.

Protecting groups of particular interest include alcohols and phenols, and the like. $R_6$ is preferably an alkyl or aralkyl group containing from 1 to 20 carbon atoms. Thus, $R_6$ can be a lower alkyl group such as methyl, ethyl or tertiary butyl, a substituted alkyl such as phthalimidomethyl, succinimidomethyl, phenacyl, substituted phenacyl such as p-bromophenacyl, a β-substituted ethyl group such as 2,2,2-trichloroethyl, 2-methylthioethyl or 2-(p-methylphenyl)-ethyl, an alkoxyalkyl group such as methoxymethyl, an aryloxyalkyl such as p-methoxyphenoxymethyl, an aralkyloxyalkyl group such as benzyloxymethyl, a substituted benzyl group such as p-nitrobenzyl, p-methoxybenzyl, 3,5-dinitrobenzyl, 2,4,6-trimethylbenzyl or 3,5-dichloro-4-hydroxybenzyl, benzhydryl or a substituted benzhydryl group such as p-methoxybenzhydryl, and the like. Preferred blocking groups are methyl, tertiary butyl, phenacyl, p-bromophenacyl, 2,2,2-trichloroethyl, p-methoxybenzyl, benzhydryl, methoxymethyl and p-methoxyphenoxymethyl.

The term "blocking group" as utilized herein is employed in the same manner and in accordance with the teaching of U.S. Pat. No. 3,697,515; the contents therein with respect to said blocking group being incorporated herein by reference.

The carboxyl groups may be regenerated from an ester by any of the usual methods; for example, acid- and base-catalysed hydrolysis (especially for silyl and stannyl esters) is generally applicable, as well as enzymicallycatalysed hydrolyses; however, aqueous mixtures may be poor solvents for these compounds and they may cause isomerizations, rearrangements, sidereactions, and general destruction, so that special methods may be desirable. Five suitable methods of deesterification are:

A—Reactions with Lewis acids: Suitable Lewis acids for reaction with the esters include trifluoroacetic acid, formic acid, hydrochloric acid in acetic acid, zinc bromide in benzene and aqueous solutions or suspensions of mercuric compounds. The reaction with the Lewis acid may be improved by addition of a nucleophile such as anisole.

B—Reduction: Suitable systems for effecting reduction are zinc/acetic acid, zinc/formic acid, zinc/lower alcohol, zinc/pyridine, palladised-charcoal and hydrogen, electrolysis, and sodium and liquid ammonia.

C—Attack by nucleophiles: Suitable nucleophiles are those containing a nucleophilic oxygen or sulphur atom for example alcohols, mercaptans and water.

D—Oxidative methods: For example, which involve the use of hydrogen perxoide and acetic acid.

E—Irradiation.

Of particular interest are the procedures involving cleavage of groups such as benzhydryl, tertiary butyl, p-bromophenacyl, p-methoxybenzyl and p-methoxyphenoxymethyl with an acid such as trifluoroacetic acid and cleavage of the 2,2,2-trichloroethyl and phenacyl groups by reaction with zinc and acetic acid.

In addition to blocking the carboxy group, it is generally preferred to block or protect any amino groups present in the starting materials since maximum yields of the desired products are obtained with such derivatives. For this purpose, the groups are preferably blocked with substituents that are readily removed. Such groups are well known in the art. For example, the amino group is most conveniently blocked by a group such as trichloroethoxycarbonyl, t-butoxycarbonyl, benzoylmethoxycarbonyl, trimethylsilyl, p-methoxybenzyloxy, o-nitrophenylthio, and the like.

The 3-phosphoranylidene starting materials, wherein B=H, are known and may be prepared in accordance with the teachings of German Offenlegungsschrift No. 2,103,014 which relate to the preparation of vinylcephalosporins as follows:

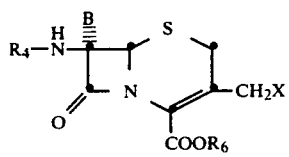

wherein X is halogen;

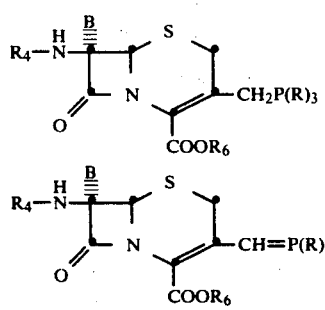

EXAMPLE A

Preparation of benzhydryl 3-carbamoyloxymethyl-7α-methoxy-7β-(2-thienylacetamido)3-cephem-4-carboxylate To a stirred slurry of 15 g. (0.0352 mole) of 3-carbamoyloxymethyl-7α-methoxy-7β-(2-thienylacetamido)3-cephem-4-carboxylate in 300 ml. acetonitrile is added 6.83 g. (0.0352 mole) of diphenyldiazomethane in 100 ml. acetonitrile during 4 hr. at 22° C. After completion of addition a small quantity (0.5 g.) of dark solid is removed by filtration and discarded. After stirring for 17 hr. at 22° the pale yellow solution is used in the nxt step directly.

The benzhydryl 3-carbamoyloxymethyl-7α-methoxy-7β-(2-thienylacetamido)3-cephem-4-carboxylate product has the following NMR spectrum: NMR(CDCl₃): 3,43 δ broad s, 2-CH₂; 3.51 δ S, 3H, O—CH₃; 3.87 δ, S, 2H,

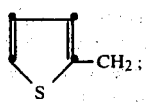

4.6–5.0 δ broad multiplet; 5.08 δ, S, 1H, C-6H; ~7.0 δ, multiplet

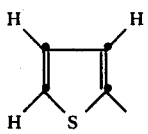

; 7.33 δ, Ph.

EXAMPLE B

Preparation of benzhydryl 3-carbamoyloxymethyl-7α-methoxy-7β-(2-thienylacetamido)2-cephem-4-carboxylate To the reaction solution obtained in Example 1 is added 1 ml. triethylamine. The solution is stirred at 22° C. for 1 hr., during which time it darkens progressively. The solvent and triethylamine are removed under reduced pressure and the residue, benzhydryl 3-carbamoyloxymethyl-7α-methoxy-7β-(2-thienylacetamido)2-cephem-4-carboxylate, is used directly in the next step. The produce weighed 20.5 g.

The product has the following NMR spectrum: NMR(CDCl₃): 3.41 δ, S, 3H, —OCH₃; 3.85 δ, S, 2H,

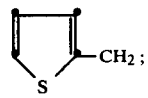

4.58 δ, S; 4.81 δ, S; 5.10 δ, S; 5.33 δ, S; 6.38 δ, sl. split broad singlet, 1 H,

6.97 δ, m.,

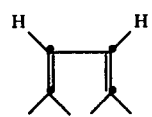

7.37 δ, S, Ph.

EXAMPLE C

Preparation of benzhydryl 3-chloromethyl-7α-methoxy-7β-(2-thienylacetamido)2-cephem-4-carboxylate The benzhydryl 3-carbamoyloxymethyl-7α-methoxy-7β-(2-thienylacetamido)2-cephem-4-carboxylate from the above reaction is dissolved in 200 ml. of methylene chloride and stirred in an ice bath under a nitrogen atmosphere. Gaseous hydrogen chloride is bubbled into the solution slowly. The progress of the reaction is followed by t.l.c. (EtOAc/PhH:1/3, silica gel G 1″×4″ plates, developed with ceric sulfate in aqueous sulfuric acid spray). Within 15 minutes the solution becomes cloudy and the reaction is over within 3 hours. The reaction mixture is evaporated under reduced pressure and flushed with methylene chloride and re-evaporated twice to remove hydrogen chloride. The benzhydryl 3-chloromethyl-7α-methoxy-7β-(2-thienylacetamido)2-cephem-4-carboxylate obtained is dissolved in 150 ml. methylene chloride, filtered to remove ammonium chloride, evaporated, and used in the next step directly.

Anal. Calcd. for $C_{28}H_{25}ClN_2O_5S_2$: C, 59.09; H, 4,43; N, 4.92 Found: C, 59.82; H, 4.54; N, 4.48.

Mass spectrum shows peaks at 568 (M+), 534, 488, 400, 358, 277, 240, 210, 204 and 167.

EXAMPLE D

Preparation of benzhydryl 3-iodomethyl-7α-methoxy-7β-(2-thienylacetamido)-2-cephem-4-carboxylate The benzhydryl 3-chloromethyl-7α-methoxy-7β-(2-thienylaceamido)2-cephem-4-carboxylate from the previous step and 75 ml. acetone is stirred in an ice bath and 8.0 g. sodium iodide in 50 ml. ice cold acetone is added. After 4 hours of stirring in an ice bath the mixture is evaporated under reduced pressure and 100 ml. of methylene chloride is added. The mixture is filtered and the solid washed well with methylene chloride. The filtrate and washings are evaporated under reduced pressure and the benzhydryl 3-iodomethyl-7α-methoxy-7β-(2-thienylacetamido)-2-cephem-4-carboxylate is obtained and used directly in the next step.

The product has the following NMR spectrum: NMR(CDCl₃): 3.43 δ, S, 3H, OCH₃; 4.10 δ, AB quartet, —CH₂I; 5.39 δ, multiplet; 6.43 δ, br.s., 1H,

7.0 δ, m.,

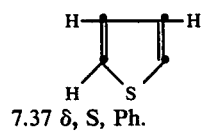

7.37 δ, S, Ph.

EXAMPLE E

Preparation of [4-diphenylmethoxycarbonyl-7α-methoxy-7β-(2-thienylacetamindo)-2-cephem-3-ylmethyl]triphenylphosphonium iodide The crude benzhydryl 3-iodomethyl-7α-methoxy-7β-(2-thienylacetamido)-22-cephem-4-carboxylate from the last reaction is dissolved in 150 ml. of ethyl acetate, cooled and stirred in an ice bath, and 18 g. of triphenylphosphine is added. Within 5 minutes the solution becomes cloudy. After stirring for 1 hour at 0° C. and 4 hours at 22° C. the liquid is decanted and the solid is washed with ethyl acetate. The residue is taken in 30 ml. methyl chloride and 300 ml. ethylacetate is added to precipitate the [4-diphenylmethoxycarbonyl-7α-methoxy-7β-(2-thienylacetamido)-2-cephem-3-ylmethyl]triphenylphosphonium idodie. The product is obtained by filtration and drying, has a m.p. 107° dec. and foams slowly as heating continues.

Anal. Calcd. for $C_{46}H_{40}N_2IO_5S_2P$: C. 59.87; H, 4.37; N, 3.04. Found: C, 59.24; H, 4.02; N, 2.57.

EXAMPLE F

Preparation of benzhydryl 3-(triphenylphosphoranylidenemethyl)-7α-methoxy-7β-(2-thienylacetamido)-3-cephem-4-carboxylate To a solution of 1.518 g. of [4-diphenylmethoxycarbonyl-7α-methoxy-7β-(2-thienylacetamido)-2-cephem-3-ylmethyl]triphenylphosphonium iodide, 18 ml. acetone and 2.4 ml. water cooled and stirred in an ice bath is added 18 drops 2N sodium hydroxide to bring the pH to 7.9–8.2. The addition of 10 ml. water causes an oil to appear which is extracted into methylene chloride, dried with anhydrous magnesium sulfate and evaporated under reduced pressure to afford 1.18 g. of benzhydryl 3-(triphenylphosphoranylidenemethyl)-7α-methoxy-7β-(2-thienylacetamido)-3-cephem-4-carboxylate.

The product had the following NMR: NMR(CDCl₃): 2.6 δ, AB quartet, 2H,

3.50 δ, S, 3H, ODH₃; 3.74 δ, S, 2H,

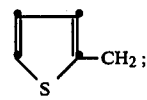

5.08 δ, 1H, S, C—6H; 5.42 δ, doublet. J=31 cps, 1H, —CH=PPh₃; 6.7–7.8 , aromatic protons, m.

EXAMPLE G

Preparation of benzhydryl 7-methoxydesacetylcephalothin

To an ethyl acetate solution (300 ml) of 7-methoxydesacetylcephalothin (4 g) is added 2.0 g of diphenyldiazomethane as a solid. After 3 hours, the reaction mixture is concentrated in vacuo to a small volume (15 ml) which is kept at 0°–5° overnight. The precipitate is collected and dried to give benzyhydryl 7-methoxydesacetylcephalothin.

EXAMPLE H

Preparation of benzhydryl 7β-thiopheneacetamido-7-methoxy-3-chloromethyl-ceph-3-ene-4-carboxylate A solution of 7-methoxydesacetylcephalothin (1.77 g., 3.4 mmoles) in tetrahydrofuran (13.5 ml) containing pyridine (0.49 ml. 6.8 mmoles) is chilled to −25°. Thionyl chloride (0.49 ml. 6.8 mmoles) in 5 ml. of tetrahydrofluran is added over a 40-minute period. After an additional hour, the mixture is poured into n-HCl which has been saturated with salt. The aqueous phase is extracted (2×30 ml) with ethyl acetate. The combined organic layers are worked with 5% sodium bicarbonate and water, dried and concentrated in vacuo to give benzhydryl 7β-thiopheneacetamido-7-methoxy-3-chloromethylceph-3-ene-4-carboxylate.

EXAMPLE I

Preparation of benzhydryl
7β-thiopheneacetamido-7-methoxy-3-iodomethylceph-3-ene-4-carboxylate A solution of benzhydryl 7β-thiopheneacetamido-7-methoxy-3-chloromethylceph-3-ene-4-carboxylate (0.25 g) in acetone (5ml) is added to a solution of sodium iodide (0.25 g) in acetone (2 ml). The mixture is allowed to stand in the dark for 2 hours, poured into brine and extracted into ethyl acetate. The orgainc layer is washed with a 5% sodium thiosulfate solution and water, dried and concentrated in vacuo to give benzhydryl 7β-thiopheneacetamido-7-methoxy-3-iodomethylceph-3-ene-4-carboxylate.

EXAMPLE J

Preparation of
[4-diphenylmethoxycarbonyl-7β-thiopheneacetamido-3-em-3-ylmethyl]triphenylphosphonium iodide To a solution of benzhydryl 7β-thiopheneacetamido-7-methoxy-3-iodomethylceph-3-ene-4-carboxylate (0.15 g) in ethyl acetate (2.5 ml) is added a solution of triphenylphosphine (0.125 g) in ethyl acetate (2 ml) over a 45-minute period in the dark. The mixture is allowed to stand another hour in an ice-bath and the product [4-diphenylmethoxycarbonyl-7β-thiopheneacetamido-ceph-3-em-3-ylmethyl]triphenylphosphonium iodide collected by filtration.

EXAMPLE K

Preparation of benzhydryl 7β-thiopheneacetamido-7-methoxy-3-(triphenylphosphoroanylidenemethyl)-ceph-3-em-4-carboxylate To a solution of [4-diphenylmethoxycarbonyl-7β-thiopheneacetamido-ceph-3-em-3-ylmethyl]triphenlyphosphonium iodide (0.1 g) in acetone:water (12 ml:2 ml) is added in an ice-bath and the pH adjusted to pH 11 with 2N sodium hydroxide. The reaction mixture is diluted with an equal volume of solvent and filtered. The precipitate is washed with acetone and ether and dried to give benzhydryl 7β-thiopheneacetamido-7-methoxy-3-(triphenylphosphoroanylidenemethyl)-ceph-3-em-4-carboxylate.

According to German Offenlegungsschrift No. 2,103,014, a 3-halomethylcephalosporin is reacted with a phosphorus-containing nucleophile e.g. a phosphine, phosphorus acid or derivative thereof to produce a phosphonium compound containing the $-CH_2P^+(R)_3$ group at the 3 position of the cephalosporin molecule.

The phosphonium compound may be converted to the corresponding phosphoranylidene compound by reaction with a base as alkali metal and alkaline earth metal hydroxides, carbonates and hydrogen carbonates e.g. sodium hydroxide or sodium hydrogen carbonate; di-sodium hydrogen phosphate; and hydrides e.g. sodium hydride.

The 3-phosphoranylidene starting materials, wherein $B=OCH_3$, are novel compounds and are the subject of copending application Ser. No. 367,256 entitled Novel Cephalosporin Compounds and Processes for their Preparation, in the name of T. R. Beattie and B. G. Christensen, Case No. 15503, Disclosure No. D 73-013, filed concurrent with the present application and now Pat. No. 3,974,151 incorporated herein by reference which discloses process for preparing the 3-phosphoranylidene as follows.

In accordance with the process for preparing the novel 3-vinyl cephalosporin compounds of the invention, the phosphoranylidene compounds are coupled with compounds containing carbonyl groups.

The carbonyl compound may, for example, be an aldehyde or ketone e.g. formaldehyde, acetaldehyde, propionaldehyde, butyraldehyde, glycoladehyde and glyoxylic esters, for example t-butyl glyoxylate.

The coupling reaction may be catalysed by a weak organic acid such as benzoic acid.

The reaction with the carbonyl compound may be carried out by vigorously stirring the components together e.g. at a temperature of from $-30°$ to $+100°$ C. When the reaction is effect at a temperature at which one or more reactant may volatilise a closed system may be used. The reaction may be effected in an inert or relatively inert solvent, for example, a halogenated hydrocarbon, e.g. methylene chloride; a hydrocarbon e.g. benzene; an acyclic or cyclic e.g. diethyl ether, tetrahydrofuran or dioxan; dimethylsulphoxide; an amide e.g. dimethylformamide or dimethylacetamide or hexamethylphosphoramide.

Representative of the carbonyl compounds that may be employed in the practice of the invention are the following:
4-chlorobenzaldehyde,
2-chlorobenzaldehyde,
4-bromobenzaldehyde,
2,4-dichloro or dibromobenzaldehyde,
4-methylthiobenzaoldehyde,
4-methyl, ethyl, propyl, i-propyl, butyl or t-butylbenzaldehyde,
4-fluorobenzaldehyde,
4-trifluoromethylbenzaldehyde,
3-trifluoromethylbenzaldehyde,
4-dimethylsulfamylbenzaldehyde,
4-methylsulfamylbenzaldehyde,
2-nitro-4-chlorobenzaldehyde,
2-methoxy-4-dichlorobenzaldehyde,
2-nitro-4-methylbenzaldehyde,
2-nitro-4-fluorobenzaldehyde,
2nitro-4-methoxybenzaldehyde,
p-anisaldehyde,
salicylaldehyde,
vanillin,
p-terephthalaldehydic acid amides (e.g. the methyl, dimethyl, methylethyl and diethylamides),
pyridine 2,3- and 4-aldehydes.
thiophene 2 or 3-aldehydes,
pyrazine aldehyde,
pyrrol-2-aldehyde,
furfural,
pyrimidine-2-aldehyde,
α and β-naphthaldehyde,
benzothiazole-2-aldehyde,
furyl-2-aldehyde,
1-methylpyrrol-2-aldehyde,
thiazole-2-aldehyde,
1-methylpyrazole-5-aldehyde,
oxazole-4-aldehyde,
1-oxypyridine 2,3 and 4-aldehydes,
5-styryl-6-ethoxyoxazole-2-aldehyde,
1-methylpyridine-4-aldehyde,
2-ethoxypyrane-3-aldehyde,
1-phenylphyridazine-6-aldehyde,
1-methylindole-3-aldehyde, 5-chlorobenzo-3-aldehyde,
thionaphthene-3-aldehyde,
benzofuran-5-aldehyde,
1-methylbenzimidazole-2-aldehyde,
7-aza-indole-3-aldehyde,
3-methylbenzopyrane,
quinoline and 8-aldehydes,
isoquinoline-4-aldehyde,
quinoxaline-2-aldehyde,
naphthyridine-2-aldehyde,
benzoxazole-2-aldehyde.

Of particular interest in the preparation of the 3-vinyl cephalosporin compounds of the invention are the following carbonyl compounds:

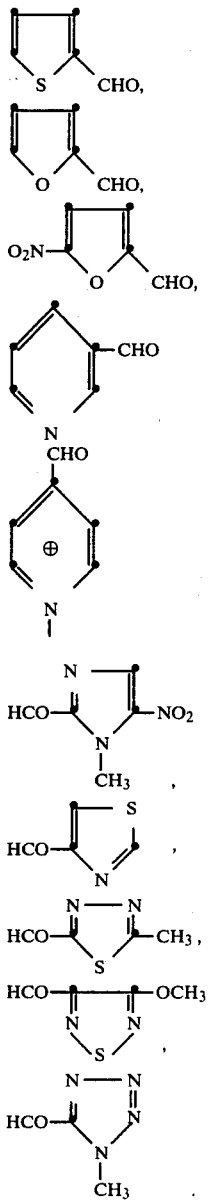

It should be noted that when the 7β-acylamido group contains an amino group it will be necessary to protect this during the various reaction stages. The protecting group is conveniently one which can be removed by hydrolysis without affecting the rest of the molecule, especially the lactam and 7β-amido linkages. The amine protecting group and the esterifying group at the 4—COOH position can be removed using the same reagent. An advantageous procedure is to remove both groups at the last stage in the sequence. Protected amine groups include urethane, arylmethyl (e.g. trityl) amino, arylmethyleneamino, sulphenylamino or enamine types. Such groups can in general be removed by one or more reagents selected from dilute mineral acids, e.g. dilute hydrochloric acid, concentrated organic acids, e.g., concentrated acetic acid, trifluoroaceti acid, and liquid hydrogen bromide at very low temperature, e.g. −80° C. A convenient protecting group is the t-butoxycarbonyl group, which is readily removed by hydrolysis with dilute mineral acid, e.g. dilute hydrochloric acid, or preferably with a strong acid (e.g. formic acid, trifluoroacetic acid or liquid HF) e.g. at a temperature of 0°–40° C. preferably at room temperature (15°–25° C.). Another convenient protecting group is the 2,2,2-trichloroethoxycarbonyl group which may be split off by an agent such as zinc/acetic acid, zinc/formic acid, zinc/lower alcohols or zinc/pyridine. The $NH_2$ group may also be protected at $NH_3^+$ by using the amino acid halide as its hydrohalide under conditions in which the amino group remains protonated.

It may be noted that the 3-vinyl compounds when prepared as described above are usually obtained as a mixture of cis- and trans- isomers about the newly formed double bond. The isomers may be separated by methods well known to the art such as preparative or column chromatography. A convenient procedure for separation of cis- and transisomers when these have different $R_f$ values on t.l.c. would be to place ~50 mg. of the mixture on an 8"×8" silica gel G preparative t.l.c. and elute with a solvent such as ethylacetate or ethyl acetate/benzene mixture. Appropriate sections are scraped off and eluted with ethyl acetate or ethyl acetate/methanol to recover the separate isomers.

The following examples illustrate the invention:

EXAMPLE 1

Preparation of benzhydryl 3-(2-pyrazinylvinyl)-7β-(2-thiopheneacetamido)-3-cephem-4-carboxylate A solution of 296 mg of pyrazine-2-carboxaldehyde [H. Rutner and P.E. Spoerri, J. Org. Chem. 28, 1998 (1963)] and 400 mg of benzhydryl 7 β-(2-thienylacetamido)-3-(triphenylphosphoranylidenemethyl)-ceph-3-em-4-carboxylate in 2 ml methylene chloride was stirred for 4 days at 22°. The solvent was removed by evaporation and the residue was chromatographed on 15 g. Baker silica gel using benzene and benzene/ethyl acetate mixture as eluent. The crude product, 374 mg, was eluted with 9–25% ethyl acetate in benzene.

The product was taken up in 2 ml methylene chloride and 6 ml hexane was added. The mixture was heated to reflux and some of the solvent was removed by evaporation under reduced pressure. The remaining solvent was siphoned from the residue. The procedure was then repeated. Drying of the residue afforded 242 mg product.

The product was dissolved in methylene chloride and chromatographed with ethyl acetate on 2-8"×8" 250 mμ thickness silica gel G preparative thin layer chromatography plates. Recovery with ethyl acetate provided 190 mg product, yield 61% characterized by n.m.r. and elemental analysis. Mass spectral analysis indicated presence of triphenylphosphine oxide as an impurity in the product.

Anal. Calcd. for $C_{32}H_{26}N_4O_4S_2$: C, 64.63; H, 4.41; N, 9.42. Found: C, 65.09; H, 4.84; N, 7.82.

NMR (CDCl$_3$)
$C_2$ 3.45 δ, 3.60 δ (m.)
$C_6$ 5.0 δ, 5.10 δ (d.d.)
$C_7$ 5.9 δ (d.d.)

EXAMPLE 2

Preparation of 3-(2-pyrazinylvinyl)-7-(2-thienylacetamido)-3-cephem-4-carboxylic acid To a solution of 147 mg of benzhydryl 3-(2-pyrazinylvinyl)-7β-(2-thienylacetamido)-3-cephem-4-carboxylate in 1.5 ml anisole at 0° was added 3 ml of cold trifluoroacetic acid. The solution was kept 10 minutes at 0° and then placed directly on a vacuum pump and evaporated. The residue was flushed with 1 ml anisole and reevaporated. The residue was triturated with 4 ml boiling ether and the ether was cooled and siphoned off. This procedure was repeated twice more. The remaining insoluble material weighed 116 mg yield 87% (calculated as mono—CF$_3$COOH salt) and was characterized by n.m.r. and electrophoresis.

NMR (DMSO-d$_6$)
$C_2$ 3.80, 4.0 δ (d.)
$C_6$ 5.28 δ (d.)
$C_7$ 5.80 δ (d.d.)

$M_{KEF}$=electrophoretic mobility relative to Keflin=0.51.

An alternative procedure for preparing the free acid involves flushing the residue with anisole and reevaporating. The flushed residue is partitioned between ethyl acetate and NaHCO$_3$, neutrals are extracted with etoac, acidified with H$_3$PO$_4$ and extracted with ethyl acetate.

In accordance with the procedures of Example 1 and 2, the following carbonyl compounds (R$_2$—CHO) are reacted with the benzhydryl cephalosporin Wittig reagent to produce the corresponding 3-vinyl cephalosporin esters which are then deblocked with trifluoroacetic acid-anisole to produce the corresponding 3-vinyl cephalosporin acids.

| Examples | Carbonyl Reagent R$_2$—CHO R$_2$ = | benzhydryl ester (COOCH(φ)$_2$) | free acid (COOH) |
|---|---|---|---|
| 3 | 2-(1-methyl-5-nitroimidazolyl) | benzhydryl 3-[2-(1-methyl-5-nitroimidazolyl)vinyl]-7-β-(2-thienylacetamido-3-cephem-4-carboxylate<br><br>NMR (CDCl$_3$)<br>$C_2$ 3.45, 3.67 δ (m.)<br>$C_6$ 4.95δ (t.)<br>$C_7$ 5.85 δ (d.d.)<br>Anal. Calcd. for $C_{32}H_{24}N_5O_6S_2$: C, 60.18; H, 3.79; N, 10.96. Found: C, 59.96; H, 4.73; N, 9.83<br>N—CH$_3$ 3.77 (s) Yield = 56% | 3-[2-(1-methyl-5-nitroimidazolyl)vinyl]-7β-(2-thienylacetamido)-3-cephem-4-carboxylic acid<br><br>NMR (DMSO-d$_6$) $M_{KEF}$ = 0.49<br>$C_2$ 3.83 δ (m.)<br>$C_6$ 5.28 δ (d.d.)<br>$C_7$ 5.77 δ (d.d.)<br>N—CH$_3$ 3.80 or 4.00 (S)<br><br>Yield = 100% |
| 4 | 2-thienyl | benzhydryl 3-(2-thienylvinyl)-7-β-(2-thienylacetamido)-3-cephem-4-carboxylate<br>NMR (CDCl$_3$)<br>$C_2$ 2.40 δ (unsym. br.d.)<br>$C_6$ 4.98, 5.10 (two d.)<br>$C_7$ 5.80 (d.d.)<br>Yield = 41% | 3-(2-thienylvinyl)-7β-(2-thienylacetamido)3-cephem-4-carboxylic acid<br><br>MS: 432 (M+), 388,208<br>$M_{KEF}$ = 0.84<br><br>Yield = 29% |
| 5 | 3-pyridyl | benzhydryl 3-(3-pyridylvinyl)-7-β-(2-thienylacetamido-3-cephem-4-carboxylate<br>NMR (CDCl$_3$)<br>$C_2$ 3.20 (br.s), 3.55 (d.)<br>$C_6$ 5.02 δ (d.d.)<br>$C_7$ 5.90 δ (m)<br>MS: 593 (M+), 547, 413, 383<br>Yield = 36% | 3-(3-pyridylvinyl)-7β-(2-thienylacetamido)3-cephem-4-carboxylic acid<br><br>MS: no 427, but 203 present<br>$M_{KEF}$ = 0.65<br><br>Yield = 29% |
| 6 | 2-(5-nitrofuryl) | benzhydryl 3-[2-(5-nitrofuryl)vinyl]-7-β-(2-thienylacetamido-3-cephem-4-carboxylate<br>NMR (CDCl$_3$)<br>$C_2$ 3.40 (unsym.d.)<br>$C_6$ 4.95 (d) and 5.25 (d)<br>$C_7$ 5.92 δ (dd)<br>Yield = 64% | 3-[2-(5-nitrofuryl)vinyl]-7β-(2-thienylacetamido)3-cephem-4-carboxylic acid<br><br>NMR (acetone-d$_6$) $M_{KEF}$ = 0.63, 0.69<br>$C_2$ 3.43 δ<br>$C_6$ 4.80 (d)<br>$C_7$ 5.48 (dd)<br>Yield = 69% |
| 7 | 2-furyl | benzhydryl 3-(2-furylvinyl)-7-β-(2-thienylacetamido)3-cephem-4-carboxylate<br>NMR (CDCl$_3$)<br>$C_2$ 3.47 δ (br.s)<br>$C_6$ 5.0 (d.d.)<br>$C_7$ 5.80 (m)<br>Yield = 59% | 3-(2-furylvinyl)-7β-(2-thienylacetamido)3-cephem-4-carboxylic acid<br><br>NMR (CDCl$_3$)<br>$C_2$ 3.55 δ (unsym.br.d.)<br>$C_6$ 5.10 δ (unsym.br.d.) $M_{KEF}$ = 0.79, 0.91<br>$C_7$ ~ 5.85 δ (m)<br>Yield = 21% |

-continued

| Examples | Carbonyl Reagent $R_2$—CHO $R_2 =$ | 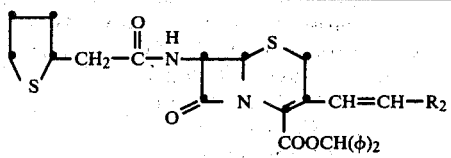 | 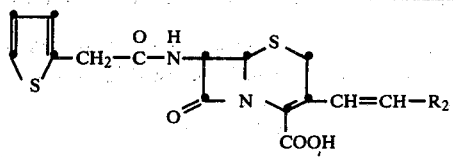 |
|---|---|---|---|
| 8 | 2-furyl | benzhydryl 3-(2-furylvinyl)-7-$\beta$-(2-thienylacetamido)3-cephem-4-carboxylate<br><br>Anal. Calcd. for $C_{32}H_{26}N_2O_5S_2$:<br>C, 65.96; H, 4.50; N, 4.81. Found:<br>C, 66.37; H, 4.46; N, 4.36 | 3-(2-furylvinyl)-7$\beta$-(2-thienyl-acetamido)3-cephem-4-carboxylic acid |
| 9 | 4-thiazolyl | benzhydryl 3-(4-thiazolylvinyl)-7-$\beta$-(2-thienylacetamido)3-cephem-4-carboxylate<br>NMR ($CDCl_3$)<br>$C_2$ 3.47 $\delta$ (unsym.d.)<br>$C_6$ 5.03 $\delta$ (d)<br>$C_7$ 5.80 $\delta$ (dd)<br>MS: 599 (M+), 432,207<br>Yield = 64% | 3-(4-thiazolylvinyl)-7$\beta$-(2-thienylacetamido)3-cephem-4-carboxylic acid<br>$M_{KEF} = 0.59$<br><br><br><br><br>Yield = 51% |
| 10 | (3-methoxy-1,2,5-thiadiazol 4-yl) | benzhydryl 3-[2-(3-methoxy-1,2,5-thiadiazol-4-yl)vinyl]-7-$\beta$-(2-thienyl-acetamido)3-cephem-4-carboxylate<br>NMR (CDCL$_3$)<br>$C_2$ 3.48 $\delta$ (unsym.br.d.)<br>$C_6$ 5.00 $\delta$ (d)<br>$C_7$ 5.80 $\delta$ (dd)<br>O—$CH_3$ 4.05 $\delta$ (s)<br>M.S. 630 (M+), 463, 419<br>Yield = 69% | 3-[2-(3-methoxy 1,2,5-thiadiazol-4-yl) vinyl]-7$\beta$-(2-thienylacetamido)3-cephem-4-carboxylic acid<br><br>NMR (acetone-$d_6$)<br>$C_2$ 3.67 $\delta$ (br.s.)<br>$C_6$ 5.22 $\delta$ (br.s)<br>vinyls 6.45 $\delta$ (d;j1 = 12 cps); 6.90 (d; j 1 = 12 cps)<br>$OCH_3$ 4.15 (s)<br>Yield = 68% |
| 11 | 2-methyl-1,3,4, thiadiazol-5-yl | benzhydryl 3-[2-(2-methyl-1,3,4, thiadiazol-5-yl)vinyl]-7-$\beta$-(2-thienyl-acetamido)-3-cephem-4-carboxylate<br>NMR ($CDCl_3$)<br>$C_2$ 3.42 $\delta$ (d)<br>$C_6$ 5.09 $\delta$ (d; J = 5 cps)<br>$C_7$ 5.96 $\delta$ (br.d.d.)<br>—$CH_3$ 2.68 $\delta$ (s.)<br>Yield = 28% | 3-[2-(2-methyl-1,3,4,thiadiazol-5-yl)-vinyl]-7$\beta$-(2-thienylacetamido)3-cephem-4-carboxylic acid<br><br>NMR ($D_2O$; as Na salt)<br>$C_2$ 3.63 $\delta$ (br.)<br>$C_6$ 5.10 $\delta$ (d.; J = 5 cps)<br>$C_7$ 5.61 $\delta$ (d.; J = 5 cps)<br>—$CH_3$ 2.68 $\delta$ (s.)<br>Yield = 52% |
| 12 | 1-methyl tetrazol-5-yl | benzhydryl 3-[2-cis-(1-methyl tetra-zol-5-yl)vinyl]-7-$\beta$-(2-thienylacet-amido)3-cephem-4-carboxylate<br>NMR ($CDCl_3$)<br>$C_2$ 3.49 $\delta$ (d)<br>$C_6$ 5.04 $\delta$ (d)<br>$C_7$ 5.83 $\delta$ (d.d.)<br>vinyls 6.07 $\delta$ (d; J = 12 cps), 6.86 $\delta$ (d,J = 12 cps)<br>N—$CH_3$ 3.76 $\delta$ (s)<br>Yield = 40% | 3-[2-cis-(1-methyl tetrazol-5-yl)vinyl]-7$\beta$-(2-thienylacetamido)3-cephem-4-carboxylic acid<br><br>NMR ($D_2O$; as Na salt)<br>$C_2$ 3.21 $\delta$ (d)<br>$C_6$ 5.01 $\delta$ (d)<br>$C_7$ 5.47 $\delta$ (d)<br>vinyls 6.21 (d; J = 12 cps), 6.81 $\delta$ (d;J = 12 cps)<br>N—$CH_3$ 3.90 $\delta$ (s)<br>Yield = 75% |
| 13 | 1-methyl tetrazol-5-yl | benzhydryl 3-[2-trans-(1-methyl tetrazol-5-yl)vinyl]-7-$\beta$-(2-thienylacet-amido)3-cephem-4-carboxylate<br>NMR ($CDCl_3$)<br>$C_2$ 3.60 $\delta$ (d)<br>$C_6$ 5.00 $\delta$ (d)<br>$C_7$ 5.96 $\delta$ (d.d.)<br>vinyls 6.50 $\delta$ (d;J = 16 cps); 8.08 $\delta$ (d; J = cps) 15 cps)<br>N—$CH_3$ 3.90 $\delta$ (s)<br>Yield = 26% | 3-[2-trans-(1-methyl tetrazol-5-yl)vinyl]-o 7$\beta$-(2-thienylacetamido)3-cephem-4-carboxylic acid<br><br>NMR ($D_2O$; as Na salt)<br><br><br>$C_6$ 5.11 $\delta$ (d)<br>$C_7$ 5.57 $\delta$ (d)<br>vinyls 6.48 $\delta$ (d;J = 15 cps); 7.58 $\delta$ (d;<br><br><br>Yield = 46% |
| 14 | 4-pyridyl | benzhydryl 3-(4-pyridylvinyl)-7-$\beta$-(2-thienylacetamido)3-cephem-4-carboxylate<br>NMR ($CDCl_3$)<br>$C_2$ 3.15 $\delta$ (broad AB)<br>3.53 $\delta$ (broad AB)<br>$C_6$ 4.95 $\delta$, 5.05 $\delta$<br>$C_7$ 5.90 $\delta$ (d.d.)<br>mass spectrum: 593 (m+), 412, 224, 167<br>UV max at 332 m$\mu$, E % = 298 Yield = 41%<br><br>benzhydryl 3-(2-pyridylvinyl)-7-$\beta$- | 3-(4-pyridylvinyl)-7$\beta$-(2-thienyl-acetamido)3-cephem-4-carboxylic acid<br>$M_{KEF} = 0.47$<br><br><br><br><br><br><br>Yield = 89% (as $CF_3$ COOH salt)<br>3-(2-pyridylvinyl)-7$\beta$-(2-thienyl- |

-continued

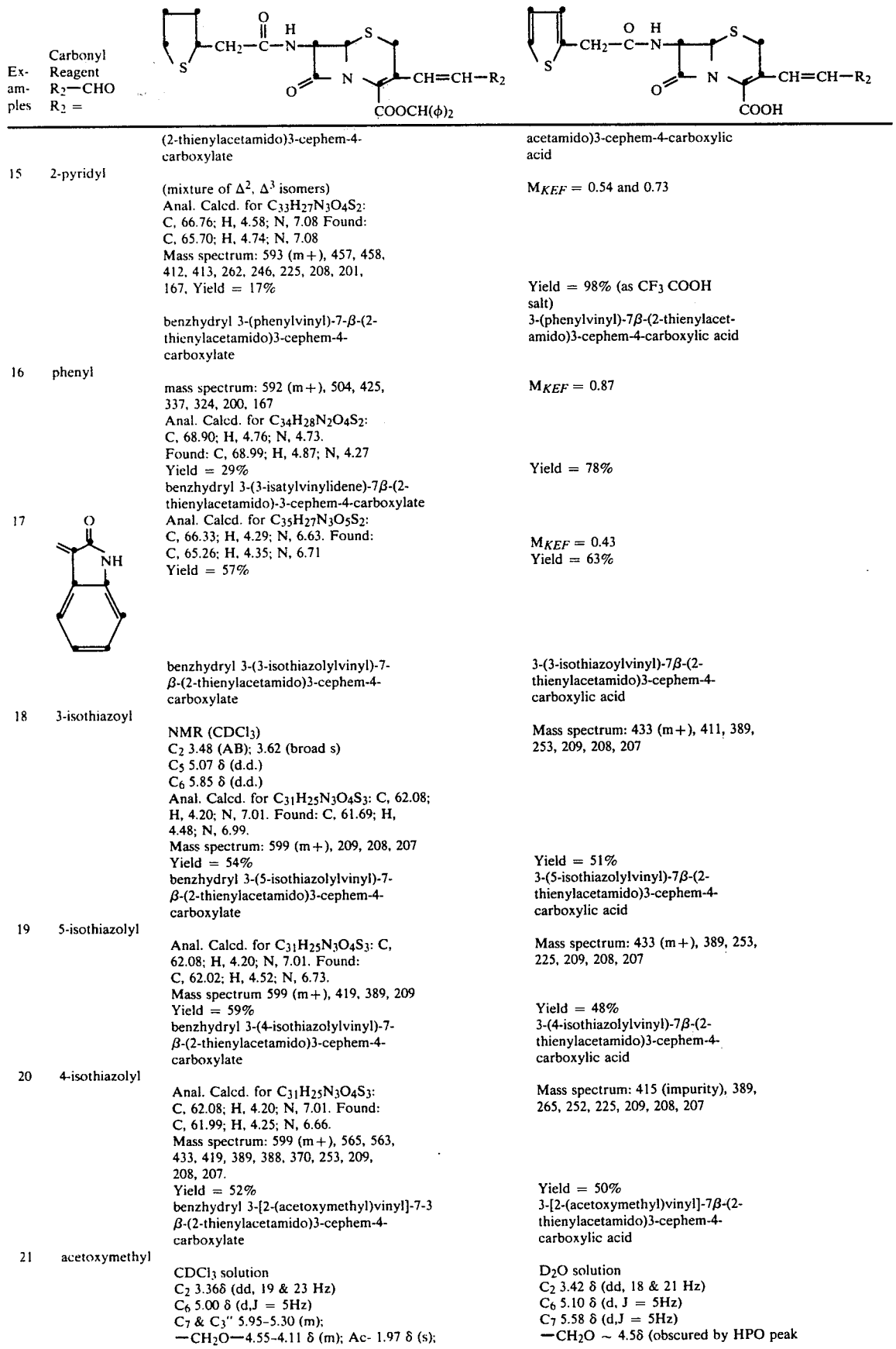

| Examples | Carbonyl Reagent $R_2$—CHO $R_2$ = | (structure with COOCH(φ)₂) | (structure with COOH) |
|---|---|---|---|
| 15 | 2-pyridyl | (2-thienylacetamido)3-cephem-4-carboxylate<br><br>(mixture of $\Delta^2$, $\Delta^3$ isomers)<br>Anal. Calcd. for $C_{33}H_{27}N_3O_4S_2$:<br>C, 66.76; H, 4.58; N, 7.08 Found:<br>C, 65.70; H, 4.74; N, 7.08<br>Mass spectrum: 593 (m+), 457, 458, 412, 413, 262, 246, 225, 208, 201, 167. Yield = 17% | acetamido)3-cephem-4-carboxylic acid<br><br>$M_{KEF}$ = 0.54 and 0.73<br><br><br><br><br>Yield = 98% (as $CF_3$COOH salt) |
| 16 | phenyl | benzhydryl 3-(phenylvinyl)-7-β-(2-thienylacetamido)3-cephem-4-carboxylate<br><br>mass spectrum: 592 (m+), 504, 425, 337, 324, 200, 167<br>Anal. Calcd. for $C_{34}H_{28}N_2O_4S_2$:<br>C, 68.90; H, 4.76; N, 4.73.<br>Found: C, 68.99; H, 4.87; N, 4.27<br>Yield = 29% | 3-(phenylvinyl)-7β-(2-thienylacetamido)-3-cephem-4-carboxylic acid<br><br>$M_{KEF}$ = 0.87<br><br><br><br>Yield = 78% |
| 17 | (isatin structure) | benzhydryl 3-(3-isatylvinylidene)-7β-(2-thienylacetamido)-3-cephem-4-carboxylate<br>Anal. Calcd. for $C_{35}H_{27}N_3O_5S_2$:<br>C, 66.33; H, 4.29; N, 6.63. Found:<br>C, 65.26; H, 4.35; N, 6.71<br>Yield = 57% | $M_{KEF}$ = 0.43<br>Yield = 63% |
| 18 | 3-isothiazoyl | benzhydryl 3-(3-isothiazolylvinyl)-7-β-(2-thienylacetamido)3-cephem-4-carboxylate<br><br>NMR (CDCl₃)<br>$C_2$ 3.48 (AB); 3.62 (broad s)<br>$C_5$ 5.07 δ (d.d.)<br>$C_6$ 5.85 δ (d.d.)<br>Anal. Calcd. for $C_{31}H_{25}N_3O_4S_3$: C, 62.08; H, 4.20; N, 7.01. Found: C, 61.69; H, 4.48; N, 6.99.<br>Mass spectrum: 599 (m+), 209, 208, 207<br>Yield = 54% | 3-(3-isothiazoylvinyl)-7β-(2-thienylacetamido)3-cephem-4-carboxylic acid<br><br>Mass spectrum: 433 (m+), 411, 389, 253, 209, 208, 207<br><br><br><br><br><br>Yield = 51% |
| 19 | 5-isothiazolyl | benzhydryl 3-(5-isothiazolylvinyl)-7-β-(2-thienylacetamido)3-cephem-4-carboxylate<br><br>Anal. Calcd. for $C_{31}H_{25}N_3O_4S_3$: C, 62.08; H, 4.20; N, 7.01. Found:<br>C, 62.02; H, 4.52; N, 6.73.<br>Mass spectrum 599 (m+), 419, 389, 209<br>Yield = 59% | 3-(5-isothiazolylvinyl)-7β-(2-thienylacetamido)3-cephem-4-carboxylic acid<br><br>Mass spectrum: 433 (m+), 389, 253, 225, 209, 208, 207<br><br><br>Yield = 48% |
| 20 | 4-isothiazolyl | benzhydryl 3-(4-isothiazolylvinyl)-7-β-(2-thienylacetamido)3-cephem-4-carboxylate<br><br>Anal. Calcd. for $C_{31}H_{25}N_3O_4S_3$:<br>C, 62.08; H, 4.20; N, 7.01. Found:<br>C, 61.99; H, 4.25; N, 6.66.<br>Mass spectrum: 599 (m+), 565, 563, 433, 419, 389, 388, 370, 253, 209, 208, 207.<br>Yield = 52% | 3-(4-isothiazolylvinyl)-7β-(2-thienylacetamido)3-cephem-4-carboxylic acid<br><br>Mass spectrum: 415 (impurity), 389, 265, 252, 225, 209, 208, 207<br><br><br><br>Yield = 50% |
| 21 | acetoxymethyl | benzhydryl 3-[2-(acetoxymethyl)vinyl]-7-3β-(2-thienylacetamido)3-cephem-4-carboxylate<br><br>CDCl₃ solution<br>$C_2$ 3.36δ (dd, 19 & 23 Hz)<br>$C_6$ 5.00 δ (d,J = 5Hz)<br>$C_7$ & $C_3''$ 5.95–5.30 (m);<br>—CH₂O—4.55–4.11 δ (m); Ac- 1.97 δ (s); | 3-[2-(acetoxymethyl)vinyl]-7β-(2-thienylacetamido)3-cephem-4-carboxylic acid<br><br>D₂O solution<br>$C_2$ 3.42 δ (dd, 18 & 21 Hz)<br>$C_6$ 5.10 δ (d, J = 5Hz)<br>$C_7$ 5.58 δ (d,J = 5Hz)<br>—CH₂O ~ 4.5δ (obscured by HPO peak |

-continued

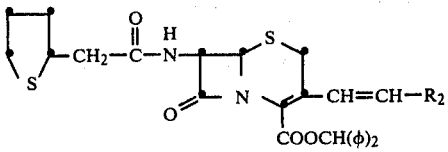

| Examples | Carbonyl Reagent R$_2$—CHO R$_2$ = | benzhydryl ester | free acid |
|---|---|---|---|
| | | C$_3$' 6.24 δ (d, 11 Hz). Yield = 27% | at 4.65 δ ); Ac- 2.10 δ (s); C$_3$' 6.18 δ (d, J = 10 Hz) C$_3$'' 5.83–5.44 δ (m) Yield = 84% |
| | | benzhydryl 3-(1-oxo-2-pyridylvinyl)-7-β-(2-thienylacetamido)3-cephem-4-carboxylate | 3-(1-oxo-2-pyridylvinyl)-7β-(2-thienylacetamido)3-cephem-4-carboxylic acid |
| 22 | 1-oxo-2-pyridyl | mixture of cis and trans isomers nmr δ 3.17 (a,C$_2$), 3.80 (s, thiophene CH$_2$), 4.92 (d, C$_6$), (s, benzhydryl), 8.18 (m, C$_6$ pyridyl). NMR (CDCl$_3$) NMR (DMSO-d) Yield = 85% 5.80 (9,C$_7$); 6.93 (9, thiophene), 7.35 | nmr δ 3.80 (S,C$_2$ and thiophene CH$_2$), 5.25 (d,C$_6$), 5.80 (m, C$_7$), 7.0–8.3 (pyridyl, thiophene & vinyls). NMR (DMSO-d$_6$) Yield = 88% |
| | | benzhydryl 3-(1-oxo-4-pyridylcisvinyl)-7-β-(2-thienylacetamido)3-cephem-4-carboxylate | 3-(1-oxo-4-pyridylcisvinyl)-7β-(2-thienylacetamido)3-cephem-4-carboxylic acid |
| 23 | 1-oxo-4-pyridyl cis | nmr δ 3.20 (a,C$_2$), 3.90 (s, thiophene CH$_2$) 5.00 (d,C$_6$), 5.83 (m,C$_7$), 6.43 (d, vinyl), 6.92 (a,thiophene), 7.345 (s, benzhydryl) 8.05 (d, pyridyl). NMR (CDCl$_3$). Yield = 45% | nmrδ 3.78 (s, C$_2$ & thiophene CH$_2$), 5.20 (d,C$_6$), 5.75 (m,C$_7$), 7.0–8.25 (pyridyl, thiophene & vinyls). NMR (DMSO-d$_6$) Yield = 95% |
| | | benzhydryl 3-(1-oxo-4-pyridyltransvinyl)-7-β-(2-thienylacetamido)3-cephem-4-carboxylate | 3-(1-oxo-4-pyridyltransvinyl)-7β-(2-thienylacetamido)3-cephem-4-carboxylic acid |
| 24 | 1-oxo-4-pyridyl trans | nmr δ 3.30 (s,C$_2$) 3.93 (s, thiophene CH$_2$) 5.00 (d, C$_6$), 5.95 (9,C$_7$), 7.25 (9, thiophene), 7.35 (s, benzhydryl), 7.95 (d, pyridyl). NMR (CDCl$_3$) Yield = 44% | nmr δ 3.80 (s,C$_2$ & thiophene CH$_2$), 5.20 (d,C$_6$), 5.77 (m,C$_7$), 7.00–8.23 (pyridyls, thiophenes & vinyls) NMR (DMSO-d$_6$). Yield = 77% |
| | | benzhydryl 3-(2-quinolylvinyl)-7-β-(2-thienylacetamido)3-cephem-4-carboxylate | 3-(2-quinolylvinyl)-7β-(2-thienylacetamido)3-cephem-4-carboxylic acid |
| 25 | 2-quinolyl | nmr δ 3.60 (α,C$_2$), 3.80 (s, thiophene CH$_2$), 4.95 (d,C$_7$ isomer), 5.20 (d,C$_7$ isomer), 5.60 (9, C$_6$ isomer), 5.95 (9,C$_6$ isomer), 6.7–8.0 (thiophene, quinolyls, vinyls & benzhydryl). NMR (CDCl$_3$). Yield = 50% | nmr δ 3.80 (s, C$_2$ & thiophene CH$_2$), 5.80 (m,C$_6$), 5.80 (m,C$_7$), 6.80–8.5 (quinolyl, thiophene & vinyls). NMR (DMSO-d$_6$) Yield = 62% |
| | | benzhydryl 3-(4-quinolylvinyl)-7-β-(2-thienylacetamido)3-cephem-4-carboxylate | 3-(4-quinolylvinyl)-7β-(2-thienylacetamido)3-cephem-4-carboxylic acid |
| 26 | 4-quinolyl | nmr δ 3.70 (α,C$_2$), 3.8 & 3.9 (s, CH$_2$-thiophene), 5.15 & 4.95 (d, C$_6$) 5.90 (m,C$_7$) 7.0–9.0 (quinolyls, thiophenes, vinyls & benzhydryl). NMR (CDCl$_3$). Yield = 67% | nmr δ 3.80 (s, C$_2$ & thiophene CH$_2$), 5.25 (m, C$_6$), 5.85 (m, C$_7$), 7.0–8.6 (quinolyls, thiophenes & vinyls) NMR (DMSO-d$_6$). Yield = 125% (some salt present) of starting material |
| | | benzhydryl 3-(3-isoquinolylvinyl)-7-β-(2-thienylacetamido)3-cephem-4-carboxylate | 3-(3-isoquinolylvinyl)-7β-(2-thienylacetamido)3-cephem-4-carboxylic acid |
| 27 | 3-isoquinolyl | nmr δ 3.7 & 3.5 (d,C$_2$) 3.85 (s, thiophene CH$_2$), 5.20 & 5.00 (d,C$_6$), 5.85 (9,C$_7$), 6.80–9.0 (quinolyls, thiophenes, benzhydryls & vinyls). NMR (CDCl$_3$) Yield = 44% | nmr δ 3.90 (m,C$_2$), 4.15 (s, CH$_2$ thiophene), 5.35 (m,C$_6$), 6.05 (m,C$_7$), 6.80–8.5 (quinolyls, thiophenes and vinyls). NMR (DMSO-d$_6$). Yield = 90% |
| | | benzhydryl 3-[trans-(1-oxy-3-pyridyl)-vinyl]-7-β-(2-thienylacetamido)3-cephem-4-carboxylate | 3-[trans-(1-oxy-3-pyridyl)vinyl]-7β-(2-thienylacetamido)3-cephem-4-carboxylic acid |
| 28 | trans-(1-oxy-3-pyridyl) | m.p. amorphous RF: 0.54 (CHCl$_3$/10% NaOH) Yield = 22% IR: 1779 cm$^{-1}$: β-lactam NMR: one vinyl proton buried under aromatics; the other a doublet centered 6.33 ppm. J$_{17}$ cps. | Yield = 80% |

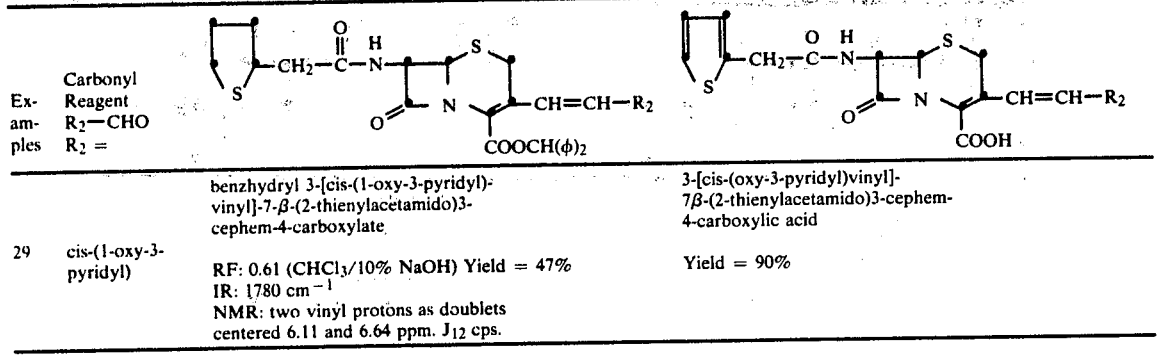

| Examples | Carbonyl Reagent $R_2$—CHO $R_2$ = | | |
|---|---|---|---|
| 29 | cis-(1-oxy-3-pyridyl) | benzhydryl 3-[cis-(1-oxy-3-pyridyl)-vinyl]-7-β-(2-thienylacetamido)3-cephem-4-carboxylate<br><br>RF: 0.61 (CHCl$_3$/10% NaOH) Yield = 47%<br>IR: 1780 cm$^{-1}$<br>NMR: two vinyl protons as doublets centered 6.11 and 6.64 ppm. J$_{12}$ cps. | 3-[cis-(oxy-3-pyridyl)vinyl]-7β-(2-thienylacetamido)3-cephem-4-carboxylic acid<br><br>Yield = 90% |

EXAMPLE 30

Preparation of benzhydryl 3-(2-thienylvinyl)-7α-methoxy-7-β-(2-thienylacetamido)-3-cephem-4-carboxylate.

A solution of 309 mg. benzhydryl-7α-methoxy-7β-(2-thienylacetamido)-3-(triphenylphosphoranylidenemethyl)-ceph-3-em-4-carboxylate and 0.30 ml. thiophene-2-carboxaldehyde in 3 ml. methylene chloride was stirred at 22° for 30 hrs. The reaction mixture was evaporated on a rotary evaporator and then on a vacuum pump to remove solvent and unreacted aldehyde. The residue was chromatographed on 7 g. Baker silica gel using benzene and benzene-ethyl acetate mixtures. The product, 122.6 mg., appeared with 10% ethyl acetate in benzene. The product was placed on 2—8"×8" prep. t.l.c. plates, eluted with ethyl acetate/benzene: ½, and the main fraction was scraped from the plates and eluted with ethyl acetate to afford 105.5 mg. product. Yield=43%.

Anal. Calcd. for C$_{33}$H$_{28}$N$_2$O$_5$S$_3$: C, 63.04; H, 4.49; N, 4.46. Found: C, 63.38; H, 4.36; N, 3.85. Mass spectrum: 628 (M+), 417, 208, 167.

EXAMPLE 31

Preparation of 3-(2-thienylvinyl)-7α-methoxy-7β-(2-thienylacetamido)-3-cephem-4-carboxylic acid.

To a solution of 84.2 mg. of benzhydryl 3-(2-thienylvinyl)-7α-methoxy-7β-(2-thienylacetamido)-3-cephem-4-carboxylate in 1 ml. anisole cooled in an ice bath was added 2 ml. ice cold trifluoroacetic acid. After 10 mins. at 0° the reaction solution was evaporated on a vacuum pump. The residue was slurried with 1 ml. anisole and reevaporated. The residue was washed twice with 4 ml. portions of boiling hexane/ether: 1/1. The insoluble residue of 66.7 mg. was dissolved in methylene chloride, filtered and reevaporated. Yield: 100%.

Nmr(CDCl$_3$): C$_2$H at 3.50; C$_6$H at 5.12 (s) and 5.19 (s); OC$\underline{H}_3$ at 3.53 (s).

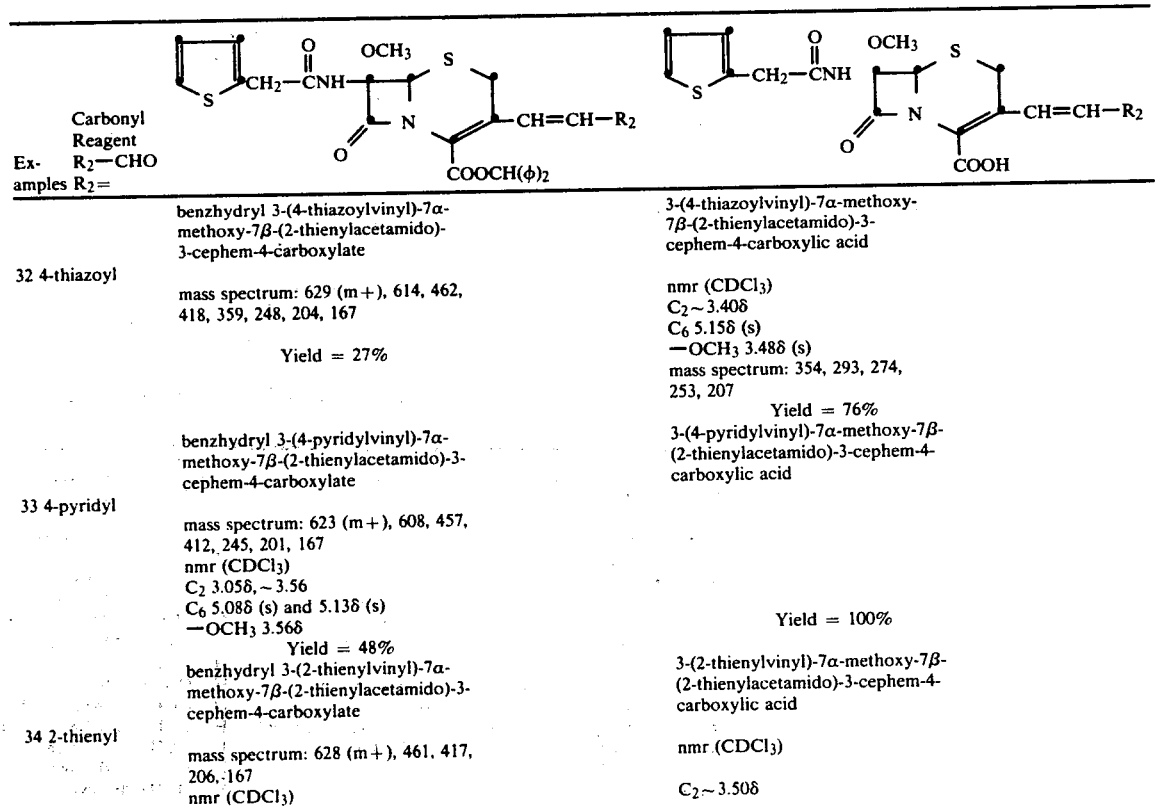

| Examples | Carbonyl Reagent $R_2$—CHO $R_2$= | | |
|---|---|---|---|
| 32 | 4-thiazoyl | benzhydryl 3-(4-thiazoylvinyl)-7α-methoxy-7β-(2-thienylacetamido)-3-cephem-4-carboxylate<br><br>mass spectrum: 629 (m+), 614, 462, 418, 359, 248, 204, 167<br><br>Yield = 27% | 3-(4-thiazoylvinyl)-7α-methoxy-7β-(2-thienylacetamido)-3-cephem-4-carboxylic acid<br><br>nmr (CDCl$_3$)<br>C$_2$∼3.40δ<br>C$_6$ 5.15δ (s)<br>—OCH$_3$ 3.48δ (s)<br>mass spectrum: 354, 293, 274, 253, 207<br>Yield = 76% |
| 33 | 4-pyridyl | benzhydryl 3-(4-pyridylvinyl)-7α-methoxy-7β-(2-thienylacetamido)-3-cephem-4-carboxylate<br><br>mass spectrum: 623 (m+), 608, 457, 412, 245, 201, 167<br>nmr (CDCl$_3$)<br>C$_2$ 3.05δ, ∼3.56<br>C$_6$ 5.08δ (s) and 5.13δ (s)<br>—OCH$_3$ 3.56δ<br>Yield = 48% | 3-(4-pyridylvinyl)-7α-methoxy-7β-(2-thienylacetamido)-3-cephem-4-carboxylic acid<br><br>Yield = 100% |
| 34 | 2-thienyl | benzhydryl 3-(2-thienylvinyl)-7α-methoxy-7β-(2-thienylacetamido)-3-cephem-4-carboxylate<br><br>mass spectrum: 628 (m+), 461, 417, 206, 167<br>nmr (CDCl$_3$) | 3-(2-thienylvinyl)-7α-methoxy-7β-(2-thienylacetamido)-3-cephem-4-carboxylic acid<br><br>nmr (CDCl$_3$)<br><br>C$_2$∼3.50δ |

-continued

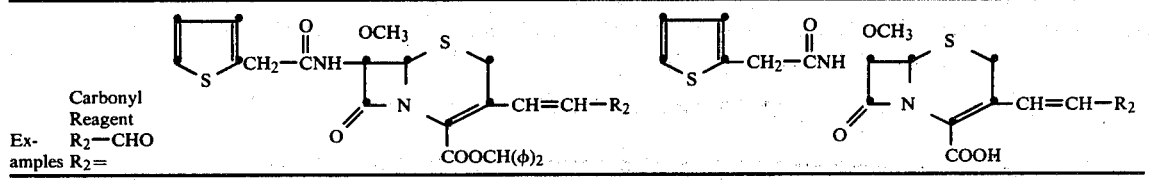

| Examples | Carbonyl Reagent R₂—CHO R₂= | (benzhydryl ester column) | (free acid column) |
|---|---|---|---|
| 35 | acetoxymethyl | C₂~3.45δ (AB)<br>C₆ 5.08δ (s) and 5.19 (s)<br>—OCH₃ 3.53δ (s)    Yield = 43%<br>benzhydryl 3-[2-(acetoxymethyl)vinyl]-7α-methoxy-7β-(2-thienylacetamido)-3-cephem-4-carboxylate<br><br>CDCl₃ solution<br>C₂~3.36δ (multiplet pattern obscured by nearby peaks);<br>C₆ 5.22δ (s);<br>—CH₂O—4.70–4.22δ (m) ; Ac— 2.00δ (s);<br>CH₃O—3.52δ (s); C₃' 6.55δ (d, 12 Hz); C₃" 5.82–5.40δ (m). | C₆ 5.12δ (s) and 5.19δ (s)<br>—OCH₃ 3.53δ (s)<br>Yield = 100%<br>3-[2-(acetoxymethyl)vinyl]-7α-methoxy-7β-(2-thienylacetamiso)-3-cephem-4-carboxylic acid<br><br>D₂O solution<br>C₂ 3.38δ (dd, 18 & 24 Hz);<br>C₆ 5.16δ (s);<br>—CH₂O— ~4.6δ (obscured by HDP peak at 4.65δ);<br>Ac = 2.13δ (s); CH₃O—3.55δ (s);<br>C₃' 6.18δ (d,J = 10Hz); C₃" 5.85–5.45 (m). |
| 36 | 2-methyl-1,3,4-thiadiazol-5-yl | Yield = 25%<br>benzhydryl 3-[2-(2-methyl-1,3,4-thiadiazol-5-yl)vinyl]-7α-methoxy-7β-(2-thienylacetamido)-3-cephem-4-carboxylate<br><br>C₂~3.5δ (obscured by nearby peaks);<br>C₆ 5.20δ (s);<br>C—CH₃ 2.72δ (s); CH₃O—3.55δ (s);<br>C₃' & C₃" amongst φ₂CH—and thienyl multiplets<br>Yield = 15% | Yield = 87%<br>3-[2-(2-methyl-1,3,4-thiadiazol-5-yl)-vinyl]-7α-methoxy-7β-(2-thienyl-acetamido)-3-cephem-4-carboxylic acid<br><br>C₂ & CH₃O—3.55 (b);<br>C₆ 5.22δ (s);<br>C—CH₃ 2.80δ; C₃', C₃", and thienyl 7.44–6.57 (m)<br>Yield = 15%<br>(Sample contaminated with aldehyde; gave overall of 15%, so must have had at least as good conversion in first step.) |
| 37 | 1-oxo-4-pyridyl | benzhydryl 3-(1-oxo-4-pyridylvinyl)-7α-methoxy-7β-(2-thienylacetamido)-3-cephem-4-carboxylate<br><br>nmrδ 3.45 (,C₂), 3.50(s, CH₃O),<br>3.90 (s, thiophene CH₂) 5.10 (s,C₆)<br>7.03 (m, thiophene), 7.35 (s, benzhydryl) 8.07 (t, pyridyl).<br>NMR (CDCl₃)<br>Yield = 52% | 3-(1-oxo-4-pyridylvinyl)-7α-methoxy-7β- (2-thienylacetamido)-3-cephem-4-carboxylic acid<br><br>nmrδ 3.40 (S, OMe), 3.75 (s,C₂),<br>3.85 (s, thiophene CH₂), 5.25 (s,C₆),<br>7.0–8.25 (pyridyl thiophenes and vinyls).<br>NMR (DMSO-d₆)<br>Yield = 75% |

Further illustrative of the 3-vinyl cephalosporins of the invention that may be prepared in accordance with procedures of Examples 1 and 2 are the following:

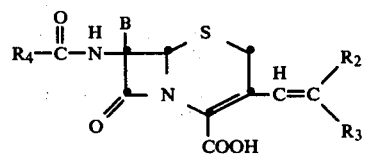

wherein B, R₂, R₃ and R₄ are as set forth above.

| Carbonyl reactant (R₂) | R₂ | R₃ | B | R₄ |
|---|---|---|---|---|
| furyl-2-aldehyde | furyl | H | H | 2-thienylmethyl |
| thiazole-2-aldehyde | thiazolyl | H | OCH₃ | benzyl |
| pyrrol-2-aldehyde | pyrrolyl | H | H | phenoxymethyl |
| thiophene-2-aldehyde | thienyl | H | H | 1-phenylpropyl |
| pyrimidine-2-aldehyde | pyrimidinyl | H | H | α-carboxybenzyl |
| pyrazinealdehyde | pyrazinyl | H | H | α-aminobenzyl |
| imidazole-2-aldehyde | imidazolyl | H | H | 2,6-dimethylphenyl |
| pyridazine-3-aldehyde | pyridazinyl | H | H | 2-furylmethyl |
| phenylaldehyde | phenyl | H | OCH₃ | 2-thienylmethyl |
| methoxyphenyl-2-aldehyde | methoxyphenyl | H | OCH₃ | 2-thienylmethyl |
| CH₃—CHO | —CH₃ | H | OCH₃ | 2-thienylmethyl |
| trifluoromethylphenyl-2-aldehyde | trifluoromethylphenyl | H | OCH₃ | 2-thienylmethyl |
| CH₃CH₂—CHO | —CH₂CH₃ | H | OCH₃ | 2-thienylmethyl |
| furyl-2-aldehyde | furyl | H | OCH₃ | 2-thienylmethyl |
| thiazole-2-aldehyde | thiazolyl | H | OCH₃ | benzyl |

| Carbonyl reactant (R$_2$) | R$_2$ | R$_3$ | B | R$_4$ |
|---|---|---|---|---|
| pyrrol-2-aldehyde | pyrrolyl | H | OCH$_3$ | phenoxymethyl |
| thiophene-2-aldehyde | thienyl | H | OCH$_3$ | 1-phenylpropyl |
| pyrimidine-2-aldehyde | pyrimidinyl | H | OCH$_3$ | α-carboxybenzyl |
| pyrazinealdehyde | pyrazinyl | H | OCH$_3$ | α-aminobenzyl |
| imidazole-2-aldehyde | imidazolyl | H | OCH$_3$ | 2,6-dimethylphenyl |
| pyridazine-3-aldehyde | pyridazinyl | H | OCH$_3$ | 2-furylmethyl |
| furyl-2-aldehyde | furyl | H | H | α-hydroxybenzyl |
| thiazole-2-aldehyde | thiazolyl | H | OCH$_3$ | α-hydroxybenzyl |
| pyrrol-2-aldehyde | pyrrolyl | H | H | α-hydroxybenzyl |
| thiophene-2-aldehyde | thienyl | H | H | α-hydroxybenzyl |
| pyrimidine-2-aldehyde | pyrimidinyl | H | H | α-hydroxybenzyl |
| pyrazinealdehyde | pyrazinyl | H | H | α-hydroxybenzyl |
| imidazole-2-aldehyde | imidazolyl | H | H | α-hydroxybenzyl |
| pyridazine-3-aldehyde | pyridazinyl | H | H | α-hydroxybenzyl |
| phenylaldehyde | phenyl | H | OCH$_3$ | α-hydroxybenzyl |
| methoxyphenyl-2-aldehyde | methoxyphenyl | H | OCH$_3$ | α-hydroxybenzyl |
| CH$_3$—CHO | —CH$_3$ | H | OCH$_3$ | α-hydroxybenzyl |
| trifluoromethylphenyl-2-aldehyde | trifluoromethylphenyl | H | OCH$_3$ | α-hydroxybenzyl |
| CH$_3$CH$_2$—CHO | —CH$_2$CH$_3$ | H | OCH$_3$ | α-hydroxybenzyl |
| furyl-2-aldehyde | furyl | H | OCH$_3$ | α-hydroxybenzyl |
| thiazole-2-aldehyde | thiazolyl | H | OCH$_3$ | α-hydroxybenzyl |
| pyrrol-2-aldehyde | pyrrolyl | H | OCH$_3$ | α-hydroxybenzyl |
| thiophene-2-aldehyde | thienyl | H | OCH$_3$ | α-hydroxybenzyl |

An alternative method for preparing the compounds of the invention involves the reaction of a 3-formyl cephalosporin with a phosphorane ylid as follows:

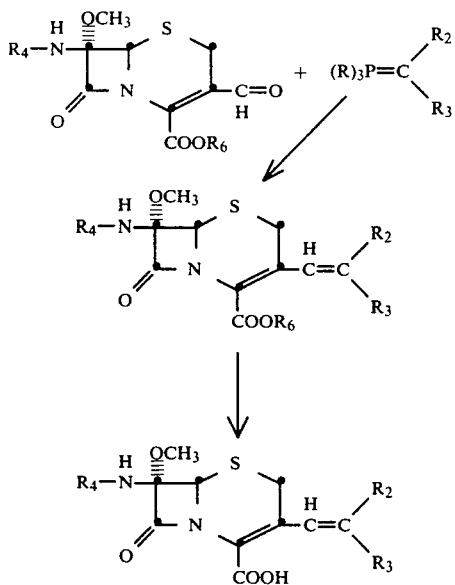

The 3-formyl cephalosporin compounds may be prepared as described in U.S. Pat. No. 3,351,596; British Patent No. 1,155,024 or Dutch patent application No. 6,815,631.

Phosphorane ylids which may be used in the reaction with 3-formyl cephalosporins include those having the general formula:

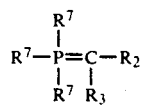

where the R$^7$ groups, which may be the same or different, are each organic groups and R$_2$ and R$_3$, are as defined above.

The nature of the groups R$^7$ is not unduly critical since the moiety =P(R$^7$)$_3$ does not form part of the cephalosporin derivative produced. R$^7$ may, for example, be C$_3$-C$_{10}$ alkyl, C$_5$- or C$_6$-cycloalkyl, aryl e.g. phenyl or substituted phenyl, di(lower alkyl) amino, etc.

The nature of R$_2$ and R$_3$ will depend on the nature of the compound to be produced and the reaction conditions involved. Preferably at least one of R$_2$ and R$_3$ is desirably an electronegative group. Representative of the electronegative groups that may be utilized are lower alkoxycarbonyl, arylloweralkoxycarbonyl, diaryl loweralkoxycarbonyl, loweralkylcarbonyl, cyano, etc.; the aryl moiety may be phenyl or substituted phenyl, e.g. halophenyl or tolyl.

The reaction of the 3-formyl cephalosporin and a phosphorane ylid may be carried out by vigorously stirring the components together, e.g. at a temperature of from −80° to +100° C., preferably from −30° to +30° C. When the reaction is effected at a temperature at which one or more reactants may volatilise, a closed system may be used. The reaction may be effected in an inert or relatively inert solvent, for example, a halogenated hydrocarbon, e.g. methylene chloride; a hydrocarbon e.g. benzene; an acyclic or cyclic ether e.g. diethyl ether, tetrahydrofuran or dioxan; an amide e.g. dimethylformamide or dimethylacetamide or hexamethylphosphoramide. The course of the reaction may be followed by thin layer chromatography and by ultraviolet spectroscopy (in general, the max shifts to higher wavelengths as the reaction produces chromophoric groups). Disappearance of the 3-formyl group is complete when no fraction on the chromatograms goes red or orange with 2,4-dinitrophenylhydrazine or when the aldehyde proton is no longer significantly intense in the nmr spectrum.

Representative of the phosphorane ylids that may be employed in the practice of the invention are the following: ethoxycarbonylmethylenetriphenylphosphorane, diphenylmethoxycarbonylmethylenetriphenylphosphorane, cyanomethylenetriphenylphosphorane, methylcarbonylmethylenetriphenylphosphorane.

Illustrative of the cephalosporins that may be produced according to the above process are the following:
3-(trans-2-ethoxycarbonylvinyl)-7-methoxy-7β-(2-thienylacetamido)ceph-3-em-4-carboxylate, 3-(trans-2-carboxyvinyl)-7-methoxy-7β-(2-thienylacetamido)-ceph-3-em-4-carboxylic acid, 3-(cis-2-cyanovinyl)-7-methoxy-7β-(2-thienylacetamido)ceph-3-em-4-carboxylic acid, 3-(trans-2-diphenylmethoxycarbonylvinyl)-7-methoxy-7β-(2-thienylacetamido)ceph-3-em-4-carboxylic acid.

Illustrative of the procedures that may be utilized to prepare the vinyl cephalosporins of the invention wherein there is a hetero atom such as P, S or N attached directly to the double bond at the 3-position is as follows:

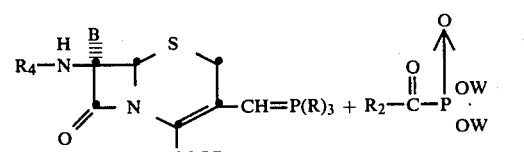

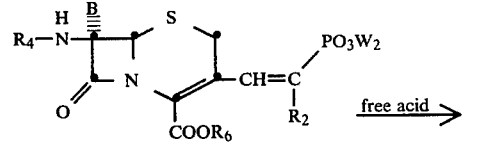

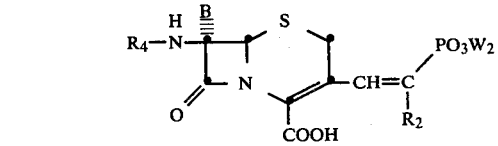

wherein W is an organo group such as alkyl (e.g. lower alkyl of 1-6 carbon atoms such as methyl, ethyl, propyl), aryl (phenyl, styryl, benzyl, phenethyl, tolyl, etc.)

II (a)

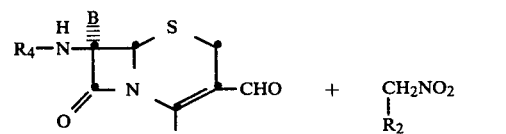

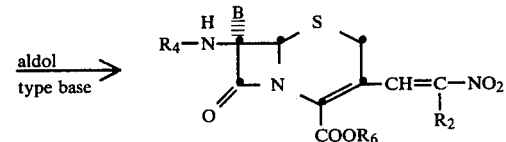

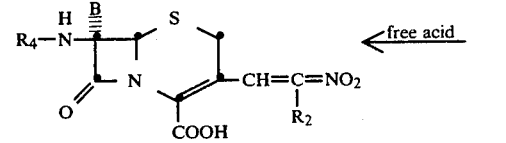

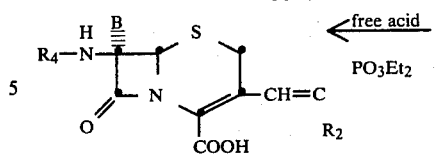

(c).

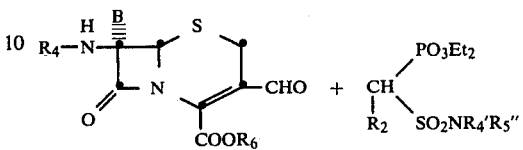

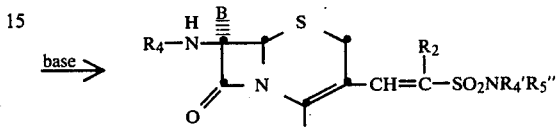

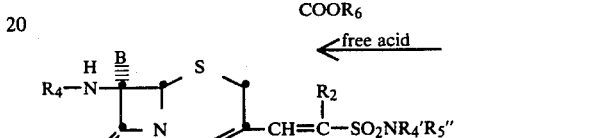

III

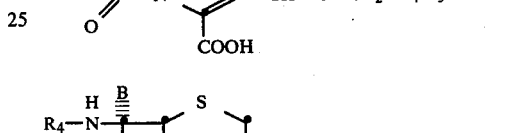

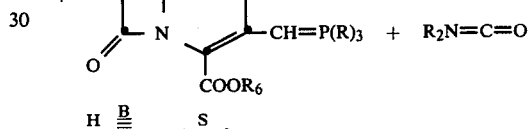

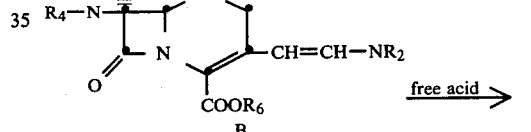

In the above procedures, $R_4$, $R_6$, $R_4'$, $R_5'$, $R_2$ are as set forth above.

The conditions under which the substitution reaction (I) proceeds is as follows:

A mixture of the cephalosporin Wittig reagent and excess of the carbonyl reagent is stirred in an inert solvent such as benzene or methylene chloride at a temperature in the range of 0°-50° until the Wittig reagent is consumed, typically a few days.

Reactions II (a) and II (b) are aldol condensations and the reaction may be carried out using conventional aldol condensation conditions well known to the art. The reaction conditions that may be employed in II (c) are typical of condensation mechanisms and including the following:

To a solution of the hetero atom substrate in an inert solvent such as tetrahydrofuran is added one molar equivalent of sodium hydride. After stirring for a short time the solution of anion is added gradually to a solution of the cephalosporin aldehyde in an inert solvent such as benzene or methylene chloride at a temperature in the range of 0°-50° and the reaction allowed to procedure until the aldehyde is consumed, typically a few days.

Reaction III involves employing a Wittig reagent and the reaction may be carried out under the conditions described above involving the coupling of the phosphoranylidene compounds with compounds containing carbonyl group, except that a longer time interval is frequently necessary to complete the reaction.

Pharmaceutically acceptable salts which may be formed using procedures well known to the art from the compounds of the invention include (a) inorganic base salts such as alkali metal, e.g. sodium and potassium, alkaline earth e.g. calcium, and organic base salts, e.g. procaine and dibenzylethylene diamine salts and (b) acid addition salts e.g. with hydrochloric, hydrobromic, sulphuric, nitric, phosphoric, toluene-p-sulphonic and methanesulphonic acids. In addition to salts, the novel cephalosporins of the invention may be administered in the form of esters, including those discussed above. Examples of esters that might be mentioned are esters of alcohols, phenols, mercaptans, and thiophenols of the general formula —$COXR_4$ wherein $R_4$ represents the radical of an alcohol or a thiol such as methyl, ethyl, tertiary butyl, a substituted alkyl such as phthalimidomethyl, succinimidomethyl, phenacyl, a substituted phenacyl for example p-bromophenacyl, a $\beta$-substituted ethyl group such as 2,2,2-trichloroethyl, 2-(p-methylphenyl)ethyl, 2-(p-methylphenyl)sulfonylethyl, 2-methylaminoethyl, 2-chloro(or bromo-)ethyl, benzyl, a substituted benzyl group such as p-nitrobenzyl, p-methoxybenzyl, 3,5-dinitrobenzyl, 2,4,6-trimethylbenzyl, 3,5-dichloro-4-hydroxybenzyl, and the like, a benzhydryl or substituted benzhydryl group such as p-methoxy-benzhydryl, an acyloxy alkyl group such as acetoxymethyl, pivaloyloxymethyl, an alkoxy group such as methoxymethyl, or a monocyclic aryl group for example phenyl or substituted phenyl such as p-nitrophenyl or 3,5-dinitrophenyl. These esters are readily prepared in accordance with processes well known in this art.

The novel 3-vinyl cephalosporins are valuable antibiotics active against various gram-positive and gram-negative bacteria and, accordingly, find utility in human and veterinary medicine. The compounds of this invention can therefore be used an antibacterial drugs for treating infections caused by gram-positive or gram-negative bacteria, for example against *Staphylococcus aureus* (penicillin resistant), *Escherichia coli, Klebsiella pneumoniae, Salmonella typhosa, Pseudomonas* and *Bacterium proteus*. The antibacterial cephalosporins of the invention may further be utilized as additives to animal feedingstuffs, for preserving foodstuffs and as disinfectants. For example, they may be employed in aqueous compositions in concentrations ranging from 0.1 to 100 parts of antibiotic per million parts of solution in order to destroy and inhibit the growth of harmful bacteria on medical and dental equipment and as bactericides in industrial applications, for example in water-based paints and in the white water of paper mills to inhibit the growth of harmful bacteria.

The products of this invention may be used alone or in combination as the active ingredient in any one of a variety of pharmaceutical preparations. These antibiotics and their corresponding salts may be employed in capsule form or as tablets, powders or liquid solutions or as suspensions or elixirs. They may be administered orally, intravenously or intramuscularly.

The compositions are preferably presented in a form suitable for absorption by the gastro-intestinal tract. Tablets and capsules for oral administration may be in unit dose presentation form, and may contain conventional excipients such as binding agents, for example, syrup, acacia, gelatin, sorbitol, tragacanth, or polyvinylpyrrolidone; fillers, for example, lactose, sugar, maize-starch, calcium phosphate, sorbitol or glycine; lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparations may be in the form of aqueous or oily suspension, solution, emulsions, syrups, elixirs, etc. or may be presented as a dry product, for reconstitution with water or other suitable vehicle before use. Such liquid preparations may contain conventional additives such as suspending agents, for example, sorbitol syrup, methyl cellulose, glucose/sugar syrup, gelatin, hydroxyethylcellulose, carboxymethyl cellulose aluminum stearate gel or hydrogenated edible fats; emulsifying agents, for example lecithin, sorbitan monooleate or acacia; non-aqueous vehicles which may include edible oils, for example, almond oil, fractionated coconut oil, oily esters, propylene glycol, or ethyl alcohol; preservatives, for example methyl or propyl p-hydroxybenzoates or sorbic acid. Suppositories will contain conventional suppository bases, e.g. cocoa butter or other glyceride.

Compositions for injection may be presented in unit dose form in ampules, or in multidose containers with an added preservative. The compositions may take such forms as suspensions, solutions, emulsions in oily or aqueous vehicles, and may contain formulatory agents such as suspending, stabilizing and/or dispersing agents. Alternatively, the active ingredient may be in powder form for reconstitution with a suitable vehicle, e.g. sterile, pyrogen-free water, before use.

The compositions may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparations may be presented as individual capsules, in liquid or semi-solid form, or may be used as drops etc. Topical applications may be formulated in hydrophobic or hydrophilic bases as ointments, creams, lotions, paints, powders, etc.

Also, in addition to a carrier, the instant compositions may include other ingredients such as stabilizers, binders, antioxidants, preservatives, lubricators, suspending agents, viscosity agents or flavoring agents and the like. In addition, there may also be included in the composition other active ingredients to provide a broader spectrum of antibiotic activity.

For veterinary medicine the composition may, for example, be formulated as an intramammary preparation in either long acting or quick-release bases.

The dosage to be administered depends to a large extent upon the condition of the subject being treated and the weight of the host, the route and frequency of administration, the parenteral route being preferred for generalized infections and the oral route for intestinal infections. In general, a daily oral dosage consists of from about 15 to about 600 mg. of active ingredient per kg. of body weight of the subject in one or more applications per day. A preferred daily dosage for adult humans lies in the range of from about 80 to 120 mg. of active ingredient per kg. of body weight. The preferred daily dosage for the compounds of the invention range from about 80 to 120 mg. of active ingredient per kg. of body weight.

The instant compositions may be administered in several unit dosage forms as, for example, in solid or liquid orally ingestible dosage form. The compositions per unit dosage, whether liquid or solid may contain from 0.1% to 99% of active material, the preferred range being from about 10–60%. The composition will generally contain from about 15 mg. to about 1500 mg. by weight of the active ingredient based upon the total weight of the composition; however, in general, it is preferable to employ a dosage amount in the range of from about 250 mg. to 1000 mg. In parenteral administration the unit dosage is usually the pure compound in a slightly acidified sterile water solution or in the form of a soluble powder intended for solution. Typical formulations of specific products are described below.

One such unit dosage form consists in mixing 120 mg. of 3-(2-pyrazinylvinyl)-7-(2-thienylacetamido)-3-cephem-4-carboxylic acid with 20 mg. of lactose and 5 mg. of magnesium stearate and placing the 145 mg. mixture into a No. 3 gelatin capsule. Similarly, by employing more of the active ingredient and less lactose, other dosage forms can be put up in No. 3 gelatin capsules and should it be necessary to mix more than 145 mg. of ingredients together, larger capsules such as compressed tablets and pills can also be prepared. The following examples are illustrative of the preparation of pharmaceutical formulations:

| TABLET | Per Tablet |
|---|---|
| 3-(2-furylvinyl)-7-(2-thienylacet-amido)-3-cephem-4-carboxylic acid | 125. mg. |
| Cornstarch, U.S.P. | 6. mg. |
| Dicalcium Phosphate | 192. mg. |
| Lactose, U.S.P. | 190. mg. |

The active ingredient is blended with the dicalcium phosphate, lactose and about half of the cornstarch. The mixture is then granulated with a 15% cornstarch paste (6 mg) and rough-screened. It is dried at 45° C. and screened again through No. 16 screens. The balance of the cornstarch and the magnesium stearate is added and the mixture is compressed into tablets, approximately 0.5 inch in diameter each weighing 800 mg.

| PARENTERAL SOLUTION | |
|---|---|
| Ampoule: | |
| 3-(2-Pyridylvinyl)-7-(2-thienylacetamido)-3-cephem-4-carboxylic acid | 500 mg. |
| Ampoule: | |
| Diluent: Sterile Water for Injection | 2 cc. |

By substituting an equivalent amount of 7-methoxy-7(α-carboxy-phenylacetamido)cephalosporanic acid for the 500 mg. of sodium salt of 3-carbamoyloxymethyl-7-methoxy-7-(2-thienylacetamido)decephalosporanate recited in the foregoing example there is also obtained a formulation suitable for parenteral administration.

| OPTHALMIC SOLUTION | |
|---|---|
| 3-(2-Pyrazinylvinyl)-7-(2-thienylacet-amido)-3-cephem-4-carboxylic acid | 100 mg. |
| Hydroxypropylmethyl Cellulose | 5 mg. |

| -continued | |
|---|---|
| Sterile Water | to 1 ml. |
| OTIC SOLUTION | |
| 3-(2-Furylvinyl)-7-(2-thienylacetamido)-3-cephem-4-carboxylic acid | 100 mg. |
| Benzalkonium Chloride | 0.1 mg. |
| Sterile Water | to 1 ml. |
| TOPICAL OINTMENT | |
| 3-(2-Pyridylvinyl)-7-(2-thienylacet-amido)-3-cephem-4-carboxylic acid | 100 mg. |
| Polyethylene Glycol 4000 U.S.P. | 400 mg. |
| Polyethylene Glycol 400 U.S.P. | 1.0 gram |

The active ingredient in the above formulations may be administered alone or in combination with other biologically active ingredients as, for example with other antibacterial agents such as lincomycin, a penicillin, streptomycin, novobiocin, gentamicin, neomycin, colistin and kanamycin, or with other therapeutic agents such as probenecid.

What is claimed is:

1. Compounds of the formula:

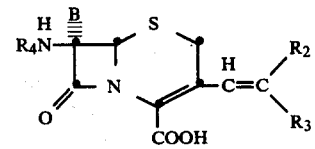

and the pharmaceutically acceptable salts and esters thereof; wherein $R_4$ is an acyl group selected from the group consisting of:
phenacetyl,
3-bromophenylacetyl,
p-aminomethylphenylacetyl,
4-carboxylmethylphenylacetyl,
4-carboxamidomethylphenylacetyl,
2furylacetyl,
5-nitrofurylacetyl,
3-furylacetyl,
2-thienylacetyl,
5-chlorothienylacetyl,
5-methoxythienylacetyl,
α-guanidino-2-thienylacetyl,
3-thienylacetyl,
4-methylthienylacetyl,
3-isothiazolylacetyl,
4-methoxyisothiazolylacetyl,
4-isothiazolylacetyl,
3-methylisothiazolylacetyl,
5-isothiazolylacetyl,
3-chloroisothiazolylacetyl,
3-methyl-1,2,5-oxadiazolylacetyl,
1,2,5-thiadiazolyl-4-acetyl,
3-methyl-1,2,5-thiadiazolyl-4-acetyl,
3-chloro-1,2,5-thiadiazolyl-4-acetyl,
3-methoxy-1,2,5-thiadiazolyl-4-acetyl,
phenylthioacetyl,
4-pyridylthioacetyl,
cyanoacetyl,
tetrazolylacetyl,
α-fluorophenylacetyl,
D-phenylglycyl,
4-hydroxy-D-phenylglycyl,
2-thienylglycyl,
3-thienylglycyl, phenylmalonyl,
3-chlorophenylmalonyl,
2-thienylmalonyl,
3-thienylmalonyl,
α-phosphonophenylacetyl,
α-sulfaminophenylacetyl,
α-hydroxyphenylacetyl,
α-tetrazolylphenylacetyl, and
α-sulfophenylacetyl;

B is hydrogen or methoxy
wherein when B is methoxy:

$R_2$ and $R_3$ may be the same or different and are each selected from the following:
(a) hydrogen;
(b) substituted and unsubstituted: lower alkyl of 1-6 carbon atoms; wherein the substituents are selected from halo, hydroxyl, $NH_2$, and $NO_2$; and wherein when B is hydrogen:

$R_2$ and $R_3$ may be the same or different and are each selected from the following:
(a) hydrogen with the proviso that both $R_2$ and $R_3$ may not be hydrogen;
(b) alkanoyloxyalkyl wherein the alkanoyl moiety has 1-6 carbon atoms and the alkyl portion has 1-6 carbon atoms.

2. A compound according to claim 1 wherein each of $R_2$ and $R_3$ is hydrogen.
3. The compound of claim 1 wherein B is methoxy.
4. The compound of claim 3 wherein each
5. The compound of claim 2 wherein B is hydrogen.
6. A compound of the formula:

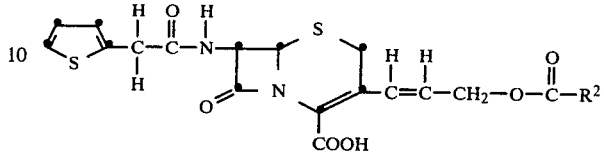

wherein $R^2$ is lower alkyl having one through six carbon atoms, and pharmaceutically acceptable salts thereof.

7. A pharmaceutical composition for the treatment of bacterial infections comprising a pharmaceutical carrier and a non-toxic, therapeutically effective amount of a compound according to claims 3, 4, 5, 1, 2 or 6.

8. A method for the treatment of bacterial infections which comprise administering to the infected host a non-toxic, therapeutically effective amount of a compound according to claims 3, 4, 5, 1, 2 or 6.

* * * * *

UNITED STATES PATENT AND TRADEMARK OFFICE
CERTIFICATE OF CORRECTION

PATENT NO. : 4,255,423
DATED : March 10, 1981
INVENTOR(S) : Beattie, et al.

It is certified that error appears in the above—identified patent and that said Letters Patent is hereby corrected as shown below:

Please correct Claim 4 as follows:

Claim 4 now reads:

"4. The compound of Claim 3 wherein each"

Claim 4 should read:

-- 4. The compound of Claim 3 wherein each of $R_2$ and $R_3$ is hydrogen. --

Signed and Sealed this

Twenty-fourth Day of May 1983

[SEAL]

Attest:

DONALD J. QUIGG

Attesting Officer

Acting Commissioner of Patents and Trademarks